US010286063B2

(12) United States Patent
De Groot et al.

(10) Patent No.: US 10,286,063 B2
(45) Date of Patent: May 14, 2019

(54) MODIFIED H7 HEMAGGLUTININ GLYCOPROTEIN OF THE INFLUENZA A/SHANGHAI/2/2013 H7 SEQUENCE

(71) Applicant: EpiVax, Inc., Providence, RI (US)

(72) Inventors: Anne S De Groot, Providence, RI (US); William D Martin, Cumberland, RI (US)

(73) Assignee: EPIVAX, INC., Providence, RI (US)

( * ) Notice: Subject to any disclaimer, the term of this patent is extended or adjusted under 35 U.S.C. 154(b) by 0 days.

(21) Appl. No.: 15/571,040

(22) PCT Filed: May 2, 2016

(86) PCT No.: PCT/US2016/030425
§ 371 (c)(1),
(2) Date: Nov. 1, 2017

(87) PCT Pub. No.: WO2016/179099
PCT Pub. Date: Nov. 10, 2016

(65) Prior Publication Data
US 2018/0161418 A1  Jun. 14, 2018

Related U.S. Application Data

(60) Provisional application No. 62/156,718, filed on May 4, 2015.

(51) Int. Cl.
| C12Q 1/70 | (2006.01) |
| A61K 39/00 | (2006.01) |
| A61K 39/12 | (2006.01) |
| A61K 39/145 | (2006.01) |
| C07K 14/005 | (2006.01) |

(52) U.S. Cl.
CPC ............ *A61K 39/145* (2013.01); *A61K 39/00* (2013.01); *A61K 39/12* (2013.01); *C07K 14/005* (2013.01); *C12Q 1/701* (2013.01); *A61K 2039/5258* (2013.01); *A61K 2039/55505* (2013.01); *A61K 2039/57* (2013.01); *A61K 2039/575* (2013.01); *C12N 2760/00034* (2013.01); *C12N 2760/16122* (2013.01); *C12N 2760/16123* (2013.01); *C12N 2760/16134* (2013.01)

(58) Field of Classification Search
CPC .................. A61K 39/145; A61K 39/12; A61K 2039/55566; A61K 39/3955; A61K 2300/00; A61K 2039/6075; A61K 39/42; C12N 2760/16134; C12N 7/00; C12N 2760/16122; C12N 2760/16034; C12N 2760/00034; C12N 2760/16111; C12N 2760/16121; C12N 2760/16151; C12N 2760/16171; C07K 14/005; C07K 16/10; C07K 14/11; C07K 16/1018
See application file for complete search history.

(56) References Cited

U.S. PATENT DOCUMENTS

| 9,555,094 B2 | 1/2017 | Kuroda et al. |
| 2007/0042002 A1 | 2/2007 | Weeks-Levy et al. |
| 2009/0018067 A1 | 1/2009 | De Groot et al. |
| 2010/0285982 A1 | 11/2010 | Golding et al. |
| 2011/0244488 A1 | 10/2011 | Liu et al. |
| 2014/0370051 A1 | 12/2014 | Chebloune et al. |
| 2014/0377299 A1 | 12/2014 | Saint-Remy |
| 2015/0044257 A1 | 2/2015 | Galloway et al. |
| 2015/0273032 A1 | 10/2015 | Losikoff et al. |
| 2018/0161418 A1 | 6/2018 | De Groot et al. |
| 2018/0161419 A1 | 6/2018 | De Groot et al. |
| 2018/0161420 A1 | 6/2018 | De Groot et al. |
| 2018/0179256 A1 | 6/2018 | De Groot et al. |

FOREIGN PATENT DOCUMENTS

| WO | 2008157419 A2 | 12/2008 |
| WO | 2013043729 A1 | 3/2013 |
| WO | 2014017493 A1 | 1/2014 |
| WO | 2014099931 A1 | 6/2014 |
| WO | 2014197723 A3 | 2/2015 |
| WO | 2015050950 A3 | 10/2015 |
| WO | 2016178811 A1 | 11/2016 |
| WO | 2016179099 A1 | 11/2016 |
| WO | 2017132550 A1 | 8/2017 |

OTHER PUBLICATIONS

Moise L, Gutierrez AH, Bailey-Kellogg C, Terry F, Leng Q, Abdel Hady KM, VerBerkmoes NC, Sztein MB, Losikoff PT, Martin WD, Rothman AL, De Groot AS. The two-faced T cell epitope: examining the host-microbe interface with JanusMatrix. Hum Vaccin Immunother. Jul. 2013;9(7):1577-86. Epub Apr. 12, 2013.*
Arunachalam, Ramaiah, Adaptive evolution of a novel avian-origin influenza A/H7N9 virus, Genomics, 2014, p. 545-553, vol. 104, Elsevier Inc.
De Groot, et al., De-immunization of Therapeutic Protein by T-Cell Epitope Modification, Development Biology, 2005, p. 171-194, vol. 122, Research Gate.
De Groot, et al., Immunoinformatic comparison of T-cell epitopes contained in novel swine-origin influenza A(H1N1) virus with epitopes in 2008-2009, convential influenza vaccine, Vaccine Science Direct, p. 5740-5747, vol. 27, Elsevier Inc.
De Groot et al. Beyond humanization and de-immunization: tolerization as a method for reducing the immunogenicity of biologics, Expert Review of Clinical Pharmacology, 2013, p. 651-662 Informa UK Ltd.
De Groot et al., Low immunoogenicity predicted for emerging avian-origin H7N9: implication for influenza vaccine design, Human Vaccines Immunotherapeutics, 2013, p. 950-956, vol. 9, Issue 5, Landes Bioscience 2013.

(Continued)

Primary Examiner — Rachel B Gill
(74) Attorney, Agent, or Firm — Dinsmore & Shohl LLP

(57) ABSTRACT

The present invention is directed to a sequence modification of the H7 hemagglutinin glycoprotein of the Influenza A/Shanghai/2/2013 H7 sequence together with vaccines derived therefrom. In addition, the invention further comprises method for improving the efficacy of vaccine antigens by modifying T cell epitopes.

11 Claims, 20 Drawing Sheets
Specification includes a Sequence Listing.

(56) References Cited

OTHER PUBLICATIONS

De Groot et al., Cross-conservation of T-cell epitopes. Now even more relevant to (H7N9) influenza vaccine design, Human Vaccines & Immunotherapeutics, Feb. 2014, p. 252-262, vol. 10, Issue 2.
Guo et al., Evasion of natural killer cells by influenza virus, Journal of Leukocite Biology Feb. 2011; p. 189-194. vol. 89, Society of Leukocyte Biology.
Guo et al., Human Antibody Responses to Avian Influenza A(H7N9) Virus, 2013, Emerging Infectious Disease, p. 192-200, 2013, vol. 20.
He et al., Integrated assessment of predicted MHC binding and cross-conservation of self reveals patterns of viral camouflage, BMC Bioinformatics, 13 pages, vol. 15:Suppl 4, 2014, Biomed Central.
Losikoff et al., HCV epitope, homogous to multiple human protein sequences, induces a regulatory T cell response in infected patients, Journal of Hepatology, p. 48-55, vol. 62, 2015.
Moise et.al., Universal H1N1 influenza vaccine development, Human Vaccines & Immunotherapeutics, p. 1598-1607, vol. 9, Issue 7, 2013.
Moise et al., The two-faced T Cell epitope Examining the host-microbe interface with JanusMatrix, Human Vaccines & Immunotherapeutics, p. 1577-1586, Landes Bioscience 2013.
Moise et al., Smarter Vaccine design will circumvent regulatory T cell-mediated evasion in chronic HIV and HCV infection, Frontiers in Microbiology 2014, Article 502, 5 pages, vol. 5.
Rosf Apweiler, et al., Reorganizing the protein space at the Universal Protein Resource (UniProt), Nucleic Acids Research, 2011, p. D71-D75, vol. 40 Published by Oxford University Press.
Su et al., Virus-Specific CD4+ Memory-Phenotype T Cells are Abundant in Unexposed Adults, Immunity, 2013, 373-383, Elsevier Inc.
US Office Action dated Jun. 13, 2018; from counterpart U.S. Appl. No. 15/847,694.
US Office Action dated Jun. 25, 2018; from counterpart U.S. Appl. No. 15/880,970.
CA Office Action dated Oct. 4, 2018; from counterpart Canadian Application No. 3001725.
PCT ISR Report and WO dated Aug. 4, 2016; from counterpart PCT Application No. PCT/US2016/027935.
PCT ISR Report dated Oct. 17, 2016; from counterpart PCT Application No. PCT/US2016/030425.
PCT IPRP and WO Report dated Nov. 7, 2017; from counterpart PCT Application No. PCT/US2015/027935.
EP Extended ISR dated Sep. 10, 2018, from counterpart PCT Application No. PCT/US2016/030425.

* cited by examiner

MNTQILVFALIAIIPTNADKICLGHHAVSNGTKVNTLTERGVEVVNATETV
ERTNIPRICSKGKRTVDLGQCGLLGTITGPPQCDQFLEFSADLIIERREGSD
VCYPGKFVNEEALRQILRESGGIDKEAMGFTYSGIRTNGATSACRRSGSS
FYAEMKWLLSNTDNAAFPQMTKSYKNTRKSPALIVWGIHHSVSTAEQTK
LYGSGNKLVTVGSSNYQQSFVPSPGARPQVNGLSGRIDFHWLMLNPNDT
VTFSFNGAFIAPDRASFLRGKSMGIQSGVQVDANCEGDCYHSGGTIISNL
PFQNIDSRAVGKCPRYVKQNTLKLATGMKNVPEIPKGRGLFGAIAGFIEN ——1
GWEGLIDGWYGFRHQNAQGEGTAADYKSTQSAIDQITGKLNRLIEKTNQ
QFELIDNEFNEVEKQIGNVINWTRDSITEVWSYNAELLVAMENQHTIDLA
DSEMDKLYERVKRQLRENAEEDGTGCFEIFHKCDDDCMASIRNNTYDHS
KYREEAMQNRIQIDPVKLSSGYKDVILWFSFGASCFILLAIVMGLVFICVK
NGNMRCTICI

FIG. 2

MNTQILVFALIAIIPTNADKICLGHHAVSNGTKVNTLTERGVEVVNATETV
ERTNIPRICSKGKRTVDLGQCGLLGTITGPPQCDQFLEFSADLIIERREGSD
VCYPGKFVNEEALRQILRESGGIDKEAMGFTYSGIRTNGATSACRRSGSS
FYAEMKWLLSNTDNAAFPQMTKSYKNTRKSPALIVWGIHHSVSTAEQTK
LYGSGNKLVTVGSSNYQQSFVPSPGARPQVNGLSGRIDFHWLMLNPNDT
VTFSFNGAFIAPDRASFLRGKSMGIQSGVQVDANCEGDCYHSGGTIISNL
PFQNIDSRAVGKCPRYVKQRSLLLATGMKNVPEIPKGRGLFGAIAGFIEN — 2
GWEGLIDGWYGFRHQNAQGEGTAADYKSTQSAIDQITGKLNRLIEKTNQ
QFELIDNEFNEVEKQIGNVINWTRDSITEVWSYNAELLVAMENQHTIDLA
DSEMDKLYERVKRQLRENAEEDGTGCFEIFHKCDDDCMASIRNNTYDHS
KYREEAMQNRIQIDPVKLSSGYKDVILWFSFGASCFILLAIVMGLVFICVK
NGNMRCTICI

FIG. 3

| FRAME START | AA SEQUENCE | FRAME STOP | HYDRO-PHOBICITY | DRB1*0101 Z-SCORE | DRB1*0301 Z-SCORE | DRB1*0401 Z-SCORE | DRB1*0701 Z-SCORE | DRB1*0801 Z-SCORE | DRB1*1101 Z-SCORE | DRB1*1301 Z-SCORE | DRB1*1501 Z-SCORE | HITS |
|---|---|---|---|---|---|---|---|---|---|---|---|---|
| 1 | CPRYVKQRS | 9 | -1.49 | -1.14 | -0.28 | -1.17 | -1.55 | 0.69 | 0.02 | -0.15 | 0.26 | 0 |
| 2 | PRYVKQRSL | 10 | -1.34 | 0.8 | 0.21 | -0.49 | 1.11 | -0.29 | 0.69 | -0.04 | -0.03 | 0 |
| 3 | RYVKQRSLL | 11 | -0.74 | -0.01 | 1.25 | -1.36 | 0.67 | 0.88 | 0.24 | 1.58 | 0.35 | 0 |
| 4 | YVKQRSLLL | 12 | 0.18 | 3.43 | 2.45 | 3.17 | 3.42 | 2.61 | 2.98 | 3.27 | 3.19 | 8 |
| 5 | VKQRSLLLA | 13 | 0.52 | 0.76 | 1.1 | 0.61 | 0.72 | 1.58 | 1.8 | 2.29 | 1.98 | 3 |
| 6 | KQRSLLLAT | 14 | -0.02 | 0.48 | 0.71 | 0.58 | 1.09 | 0.45 | 1.32 | 0.52 | 1.47 | 0 |
| 7 | QRSLLLATG | 15 | 0.37 | 0.69 | 0.33 | 0.75 | -0.76 | 1.76 | 1.8 | 0.76 | 0.52 | 2 |
| 8 | RSLLLATGM | 16 | 0.97 | 1.03 | 0.97 | 0.39 | 0.36 | -0.39 | -0.43 | 1.17 | 0.91 | 0 |
| 9 | SLLLATGMK | 17 | 1.03 | 0.85 | 0.52 | 1.19 | 0.54 | 1.07 | 1.1 | -0.34 | 0.81 | 0 |
| 10 | LLLATGMKN | 18 | 0.73 | 1.86 | 1.09 | 1.84 | 1.15 | 1.78 | 1.32 | 0.12 | 2.27 | 4 |
| 11 | LLATGMKNV | 19 | 0.78 | 0.48 | -0.65 | -0.09 | 1.38 | -0.03 | -0.35 | 0.39 | 0.37 | 0 |
| 12 | LATGMKNVP | 20 | 0.18 | -0.91 | 0.81 | -0.51 | -0.91 | 0.05 | 0.49 | -0.43 | 0.13 | 0 |
| 13 | ATGMKNVPE | 21 | -0.63 | 0.67 | 0.64 | 0.64 | -0.08 | 0.98 | 0.02 | 0.48 | 0.11 | 0 |

| SUMMARIZED RESULTS | | DRB1*0101 | DRB1*0301 | DRB1*0401 | DRB1*0701 | DRB1*0801 | DRB1*1101 | DRB1*1301 | DRB1*1501 | TOTAL |
|---|---|---|---|---|---|---|---|---|---|---|
| MAXIMUM SINGLE Z SCORE | | 3.43 | 2.45 | 3.17 | 3.42 | 2.61 | 2.98 | 3.27 | 3.19 | — |
| SUM OF SIGNIFICANT Z SCORES | | 5.29 | 2.45 | 5.01 | 3.42 | 6.15 | 6.59 | 5.57 | 7.45 | 41.93 |
| COUNT OF SIGNIFICANT Z SCORES | | 2 | 1 | 2 | 1 | 3 | 3 | 2 | 3 | 17 |

| TOTAL ASSESSMENTS PERFORMED:104 | HYDROPHOBICITY:-0.37 | EpiMatrix SCORE:31.22 | EpiMatrix SCORE (W/O FLANKS): 31.22 |
|---|---|---|---|

FIG. 4

(i) A/SHANGHAI/2/2013 H7 CLUSTER 321
CPRYVKQRSLLLATGMKNVPE
             |  |      — 1
             |  |      — 2
                |      — 3
             ▼  ▼
CPRYVKQNTLKLATGMKNVPE
(ii) EPIVAX MOD1 H7 HEMAGLUTTININ

FIG. 6

| FRAME START | FRAME STOP | AA SEQUENCE | HYDRO-PHOBICITY | DRB1*0101 Z-SCORE | DRB1*0301 Z-SCORE | DRB1*0401 Z-SCORE | DRB1*0701 Z-SCORE | DRB1*0801 Z-SCORE | DRB1*1101 Z-SCORE | DRB1*1301 Z-SCORE | DRB1*1501 Z-SCORE | HITS |
|---|---|---|---|---|---|---|---|---|---|---|---|---|
| 1 | 9 | CPRYVKQNT | -1.37 | -1.39 | -1.48 | -1.78 | -1.21 | 0.12 | -0.62 | -1.32 | 0.02 | 0 |
| 2 | 10 | PRYVKQNTL | -1.22 | 0.68 | 0.46 | -0.25 | 1.45 | -0.16 | 0.44 | -0.11 | 0.34 | 0 |
| 3 | 11 | RYVKQNTLK | -1.48 | -0.34 | 0.32 | -0.1 | -0.51 | 0.58 | -0.57 | 0.77 | -0.23 | 0 |
| 4 | 12 | YVKQNTLKL | -0.56 | 3.06 | 2.28 | 3.18 | 2.81 | 2.43 | 2.81 | 3.11 | 2.55 | 8 |
| 5 | 13 | VKQNTLKLA | -0.21 | 0.97 | 1.51 | 0.95 | 1.06 | 1.62 | 2.01 | 1.7 | 1.41 | 2 |
| 6 | 14 | KQNTLKLAT | -0.76 | 0.49 | -0.1 | 0.22 | 0.54 | 1 | -0.89 | 0.86 | 1.34 | 0 |
| 7 | 15 | QNTLKLATG | -0.37 | 0.15 | -0.22 | 0.23 | -1.29 | 1.19 | 1.26 | 0.23 | 0.01 | 0 |
| 8 | 16 | NTLKLATGM | 0.23 | 0.24 | 0.63 | -0.41 | 0.33 | -0.02 | -0.77 | 1.07 | -0.44 | 0 |
| 9 | 17 | TLKLATGMK | 0.19 | 0.8 | 0.05 | 1.15 | 0.49 | 1.02 | 1.05 | -0.8 | 0.36 | 0 |
| 10 | 18 | LKLATGMKN | -0.12 | 1.99 | 1.23 | 1.98 | 1.28 | 1.92 | 1.46 | 0.25 | 2.41 | 4 |
| 11 | 19 | KLATGMKNV | -0.08 | -0.26 | -1.53 | -0.81 | 0.65 | -0.81 | -1.11 | -0.48 | -0.48 | 0 |
| 12 | 20 | LATGMKNVP | 0.18 | -0.91 | 0.81 | -0.51 | -0.91 | 0.05 | 0.49 | -0.43 | 0.13 | 0 |
| 13 | 21 | ATGMKNVPE | -0.63 | 0.67 | 0.64 | 0.64 | -0.08 | 0.98 | 0.02 | 0.48 | 0.11 | 0 |

| SUMMARIZED RESULTS | | | | DRB1*0101 | DRB1*0301 | DRB1*0401 | DRB1*0701 | DRB1*0801 | DRB1*1101 | DRB1*1301 | DRB1*1501 | TOTAL |
|---|---|---|---|---|---|---|---|---|---|---|---|---|
| MAXIMUM SINGLE Z SCORE | | | | 3.06 | 2.28 | 3.18 | 2.81 | 2.43 | 2.81 | 3.11 | 2.55 | — |
| SUM OF SIGNIFICANT Z SCORES | | | | 5.05 | 2.28 | 5.15 | 2.81 | 4.36 | 4.82 | 4.81 | 4.96 | 34.24 |
| COUNT OF SIGNIFICANT Z SCORES | | | | 2 | 1 | 2 | 1 | 2 | 2 | 2 | 2 | 14 |

| TOTAL ASSESSMENTS PERFORMED: 104 | HYDROPHOBICITY: -0.68 | EpiMatrix SCORE: 23.53 | EpiMatrix SCORE (W/O FLANKS): 23.53 |
|---|---|---|---|

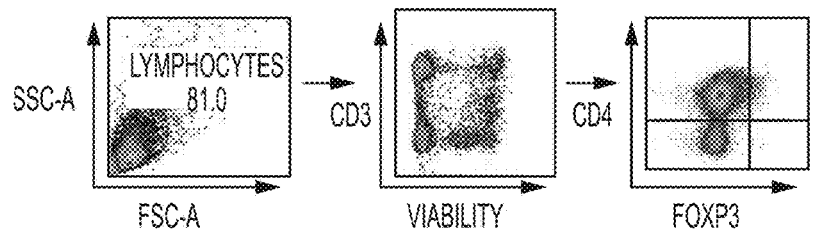
FIG. 14A
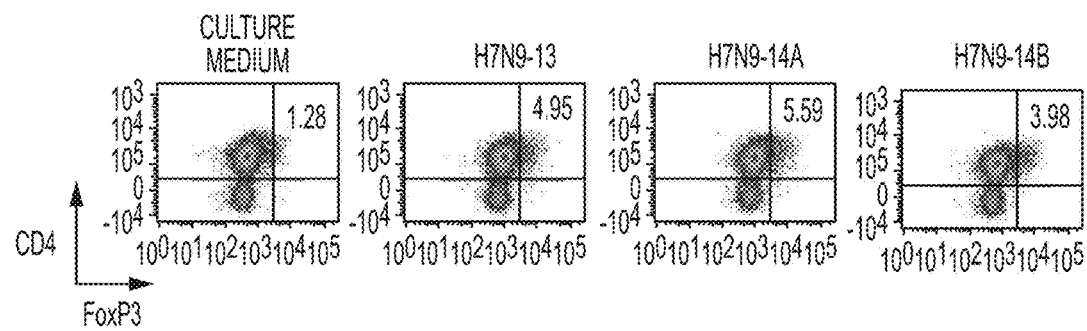
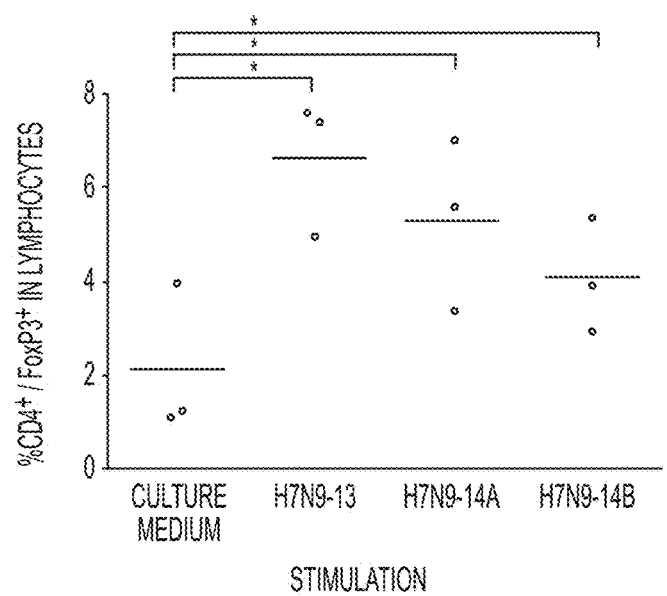
FIG. 14B

EXAMPLE EpiBar

ACCESSION: INFLUENZA ~ SEQUENCE: HA306-318

| FRAME START | AA SEQUENCE | FRAME STOP | DRB1*0101 Z-SCORE | DRB1*0301 Z-SCORE | DRB1*0401 Z-SCORE | DRB1*0701 Z-SCORE | DRB1*0801 Z-SCORE | DRB1*1101 Z-SCORE | DRB1*1301 Z-SCORE | DRB1*1501 Z-SCORE | HITS |
|---|---|---|---|---|---|---|---|---|---|---|---|
| 306 | PRYVKQNTL | 314 | | | | 1.45 | | | | | 0 |
| 307 | RYVKQNTLK | 315 | | | | | | | | | 0 |
| 308 | YVKQNTLKL | 316 | 3.06 | 2.28 | 3.18 | 2.81 | 2.43 | 2.81 | 3.11 | 2.55 | 8 |
| 309 | VKQNTLKLA | 317 | | 1.51 | | | 1.62 | 2.01 | 1.7 | 1.41 | 2 |
| 310 | KQNTLKLAT | 318 | | | | | | | | 1.34 | 0 |

ASSESSMENTS PERFORMED: 40 DEVIATION FROM EXPECTATION: 21.82

Z SCORE INDICATES THE POTENTIAL OF A 9-MER FRAME TO BIND TO A GIVEN HLA ALLELE;
THE STRENGTH OF THE SCORE IS INDICATED BY THE BLUE SHADING AS SHOWN BELOW:

| CLUSTER REGIONS OUTLINED | TOP 1% | TOP 5% | TOP 10%* | *REMAINING SCORES MASKED |
|---|---|---|---|---|

ALL SCORES IN THE TOP 5% ARE CONSIDERED "HITS". *NO HITS BELOW 10% ARE MASKED FOR SIMPLICITY

MODIFIED H7 HEMAGGLUTININ GLYCOPROTEIN OF THE INFLUENZA A/SHANGHAI/2/2013 H7 SEQUENCE

CROSS REFERENCE TO RELATED APPLICATIONS

This application is a National Stage Application of PCT International Patent Application No. PCT/US2016/030425 filed on May 2, 2016, under 35 U.S.C. § 371, which designates the United States and claims priority to U.S. Provisional Patent Application No. 62/156,718, filed on May 4, 2015. The entire contents of all of the above-listed applications are incorporated by reference herein.

STATEMENT AS TO RIGHTS TO INVENTIONS MADE UNDER FEDERALLY SPONSORED RESEARCH AND DEVELOPMENT

This invention was made with United States Government financial support under Grant No. AI082642 awarded by the National Institutes of Health. The United States Government may have certain rights in this invention.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Sep. 21, 2018, is named "SEQUENCE LISTING MODIFIED H7_ST25" and is 20 KB bytes in size.

BACKGROUND

The present invention is a sequence modification of the H7 hemagglutinin glycoprotein of the Influenza A/Shanghai/2/2013 H7 sequence.

The discordant immunogenicity of vaccines developed for two distinct emerging influenza A viruses (IAV), 2009 pandemic H1N1 (A(H1N1)pdm09) and H7N9 avian influenza (H7N9), provided an opportunity to evaluate the role of T cells in the development of effective humoral immune response. For example, although A(H1N1)pdm09 was highly transmissible and spread to more than 200 countries within 12 months of emergence due to the lack of pre-existing antibodies, morbidity and mortality due to the A(H1N1)pdm09 influenza were lower than expected, presumably due to pre-existing T cell responses among individuals exposed to or vaccinated with seasonal A(H1N1) strains. H7N9's emergence in China in 2013 was associated with much higher lethality. Due to concerns about its lethality and pandemic potential, H7N9 vaccines were prioritized for production, and vaccines were developed.

Influenza vaccines can call upon memory T cells to generate protective immunity and stimulate antibody response in the absence of adjuvants; thus, usually only one vaccination is required to generate protective immunity to seasonal influenza strains. Conventional recombinant H7 hemagglutinin vaccines produced to address the re-emergence of avian-origin H7N9 influenza (for which cross-reactive humoral immunity is presumed to be absent) in China have proven to have poor efficacy compared to other subunit and seasonal influenza vaccines. In stark contrast with A(H1N1)pdm09, un-adjuvanted H7N9 vaccines were poorly antigenic and vaccination with un-adjuvanted H7N9 hemagglutinin (HA) resulted in hemagglutination inhibition (HI) seroconversion rates of only 6% and 15.6% in Phase I clinical trials (as compared to 89% for similar un-adjuvanted A(H1N1)pdm09 subunit vaccines). Clinical trials of these vaccines have required the use of adjuvant to increase the antigenicity of these vaccines to acceptable standards, however, adjuvants are not used in standard seasonal influenza vaccines in the United States. Even when two doses of H7N9 vaccine were administered with adjuvant to generate new memory T helper cells to the novel virus, only 59% of subjects sero-converted in a recent Phase II clinical trial. The development of neutralizing antibodies to H7N9 is also delayed in H7N9-infected humans when compared to the typical immune response to other IAV infections and IgG avidity to H7N9 HA is significantly lower. In clinical trials of other H7 subtypes, an attenuated H7N1 vaccine elicited low HI titers, and an inactivated subunit H7N7 vaccine was poorly immunogenic.

H7 HA appears to be uniquely non-antigenic. The observed human antibody response to a related H7 HA in the H7N7 outbreak in 2003 in the Netherlands was also diminished in HI titer. Taken together, these studies suggest that adaptive immune responses to H7N9 infection may be diminished and delayed, even in the context of natural infection.

$CD4^+$ T cells provide help to B cells, supporting isotype conversion and affinity maturation; thus, diminished and delayed antibody responses to H7 HA suggest that T cell help was limited or abrogated. There are fewer $CD4^+$ T helper epitopes in the H7N9 sequences than in other IAV. Similar patterns of epitope deletion have been observed in chronic ('hit-and-stay') viruses that have adapted to the human host, such as Epstein Barr virus (EBV) and Herpes simplex virus (HSV), but not in acute ('hit-and-run') viruses Immune escape mediated by epitope deletion is a well-established mechanism of viral pathogenesis for human immunodeficiency virus (HIV) and hepatitis C virus (HCV), but this escape mechanism has not been previously described for influenza.

Another means by which H7N9 may minimize host response is to adopt 'immune camouflage', a new mechanism of immune escape identified by our group. T cell epitopes derived from pathogens that have high T cell receptor (TCR) 'cross-conservation' with human sequences can be identified using JanusMatrix (EpiVax, Providence, R.I., USA), an algorithm that compares TCR-facing patterns of $CD4^+$ T cell epitopes to sequence patterns present in the human genome. JanusMatrix is a homology analysis tool that considers aspects of antigen recognition that are not captured by raw sequence alignment. Commensal viruses contain a significantly higher number of these JanusMatrix-defined 'human-like' T cell epitopes than viruses that do not establish chronic infections in humans.

HCV contains an epitope that is highly cross-conserved with self and significantly expands T regulatory cells (Tregs) in vitro. T cells that respond to this peptide exhibit markers that are characteristic of Tregs and actively suppress bystander effector T cell responses in vitro. The striking difference between chronic-disease viruses, which appear to have many such epitopes, and acute-disease, pathogenic viruses, suggests that immune camouflage may be an important method by which certain human pathogens escape adaptive immune response.

Pre-existing heterotypic T cell memory specific for epitopes contained in the new flu strain obviate the need for adjuvants and effective antibody titers may develop following a single dose as was observed for A(H1N1)pdm09

(Greenberg M E et al., *N. Engl. J. Med.*, 361:2405-13, 2009). While T cell epitopes that recall pre-existing immunity may help protect against multiple viral subtypes as was observed for A(H1N1)pdm09 influenza (Laurie K L et al., *J. Infect. Dis.*, 202:1011-20, 2010), epitopes that resemble host sequences may be detrimental to immunity.

In a retrospective analysis of published viral epitopes in a large epitope database, greater human cross-conservation was associated with absent or regulatory T cell responses (He L et al., *BMC Bioinformatics*, 15:S1, 2014). Taken together, these findings demonstrate that certain human pathogens may evolve to contain T cell epitopes in their proteomes that resemble important human regulatory T cell epitopes ('immune camouflage').

The T cell epitope profile of H7N9 (few effector T cell epitopes and many cross-conserved epitopes) is much closer to these 'hit-and-stay' viruses than viruses that 'hit-and-run'. Although human-to-human transmission of H7N9 is rare, the virus has been noted to have a 'mammalian signature'. Cases of limited human-to-human transmission have been reported (Gao H N et al., *Int. J. Infect. Dis.*, 29C:254-8, 2014). Human-to-human transmission of H7N9 may occur more frequently than suspected making it harder to detect due to low titers of antibody. The discovery of human-like epitopes in the H7N9 proteome raises an important question about the origin and evolution of H7N9 and the duration of its circulation in human beings or other mammals.

The H7N9 genome (made publicly available on the GISAID website on Apr. 2, 2013) was analyzed using an immunoinformatics toolkit. The analysis indicated that the H7 HA had fewer than expected T-cell epitopes and would be poorly immunogenic.

Accordingly, a need remains for influenza vaccines with greater efficacy to address the re-emergence of avian-origin H7N9 influenza in China without the use of adjuvant to increase the antigenicity.

BRIEF SUMMARY

The present invention provides a sequence modification of the H7 hemagglutinin glycoprotein of the Influenza A/Shanghai/2/2013 H7 sequence (SEQ ID NO: 2). Three amino acids changed in the wild type virus resulted in a sequence with less cross reactivity while not compromising immunogenicity. Moreover, the invention provides vaccines with greater efficacy with or without the use of an adjuvant.

In one embodiment, the present invention provides a nucleic acid that encodes the modified H7 hemagglutinin glycoprotein of the Influenza A/Shanghai/2/2013 H7 sequence (SEQ ID NO: 2) together with a vector comprising the nucleic acid and further a cell comprising the vector.

In another embodiment, a method for vaccinating against influenza by administering to a subject a composition comprising one or more polypeptides comprising the selected modified amino acid sequence SEQ ID NO: 3, the entire amino acid sequence of SEQ ID NO: 2 or a fragment thereof containing SEQ ID NO: 3, is provided.

In a further embodiment, said method for vaccinating against influenza utilizes an adjuvant.

In another embodiment, the method for vaccinating is against influenza Avian-origin H7N9 influenza.

In yet another embodiment, the instant invention provides a method for enhancing an anti-H7 antibody response comprising administering a composition comprising one or more polypeptides comprising the amino acid sequence of SEQ ID NO: 3 or the entire amino acid sequence of SEQ ID NO: 2.

In the aforementioned embodiment, an adjuvant may be used.

In a further embodiment, the present invention includes a kit comprising one or more polypeptides comprising the amino acid sequence of SEQ ID NO: 3 or one or more polypeptides comprise the entire amino acid sequence of SEQ ID NO: 2 and may also further contain an adjuvant.

In yet another embodiment, a method for improving the efficacy of vaccine antigens against select pathogens comprising the steps of: (a) identifying constituent T cell epitopes which share TCR contacts with proteins derived from either the human proteome or the human microbiome; and (b) making modifications to said T cell epitopes so as to either reduce MHC binding and/or reduce homologies between TCR contacts of said target T cell epitope and the human proteome or the human microbiome; provided that the functional correspondence between antibodies raised against said vaccine antigens and related wild type proteins, is provided.

In another aspect of the previous embodiment, the epitopes engage either regulatory T cells or fail to engage effector T cells.

A further aspect of the same embodiment provides for modifications that replace an amino acid sequence of said target T cell epitope with an amino acid sequence of a different T cell epitope.

In yet another expansion of the same embodiment, modifications are made to reduce the homology between said target T cell epitope and either the human genome, the human microbiome or both.

Further modifications of the same embodiment provide that the functional correspondence between antibodies raised against said vaccine antigens and related wild type protein is not interrupted by the modifications made to said target T cell epitope; the replaced amino acid sequence of said target T cell epitope is derived from a variant sequence of the vaccine antigens; the replaced amino acid sequence of said target T cell epitope is derived from an amino acid sequence of a protein that is homologous to said target T cell epitope; and/or the replaced amino acid sequence is present in a strain or Glade of the pathogen containing the vaccine antigen and the modified T cell epitope induces responses from memory T cells in subjects not previously exposed to the virus resulting in said vaccine antigens.

In yet other forms of the prior embodiment, the subject is a human subject who has been previously exposed to the pathogen through vaccination or natural infection.

Additional elements of the same embodiment include antigens that target the HA protein of the influenza virus which may be influenza A, influenza B or influenza C, more particularly influenza A and its serotypes H1N1, H2N2, H3N2, H5N1, H7N7, H1N2, H9N2, H7N2, H7N3, H10N7 or H7N9, and most particularly the H7N9 serotype influenza A/Shanghai/2/2013.

A further embodiment of the present invention provides for a method for improving the efficacy of vaccine antigens against select pathogens comprising the steps of: (a) identifying amino acid residues found in a vaccine antigen which would be good candidates for modification while preserving functional correspondence between antibodies raised against said vaccine antigens and its related wild type proteins; and (b) replacing said amino acid residues with T cell epitopes thereby modifying said vaccine antigen.

The previous embodiment may utilize T cell epitopes derived from a variant sequence of the vaccine antigen; an inserted amino acid sequence of said T cell epitope derived from an amino acid sequence of a protein that is homologous to said modified vaccine antigen; T cell epitopes found in another strain or Glade of the pathogen containing the vaccine antigen; and T cell epitopes are known to induce memory cell responses in subjects.

In yet further variations of the last embodiment include a human subject who has been previously exposed to the pathogen either through vaccination or natural infection.

The same embodiment may also provide for vaccine antigens that target the HA protein of the influenza virus wherein the influenza virus is influenza A, influenza B or influenza C, more preferred influenza A and its serotypes H1N1, H2N2, H3N2, H5N1, H7N7, H1N2, H9N2, H7N2, H7N3, H10N7 or H7N9, more particularly the H7N9 serotype, and most particularly influenza A/Shanghai/2/2013.

In another embodiment of the immediate invention, a method for improving the efficacy of vaccine antigens against influenza A is provided comprising the steps of: (a) acquiring a strain of said influenza A; (b) identifying a putative T cell epitope present in said influenza A strain wherein said T cell epitope shares TCR contacts with a number of proteins and said T cell epitope induces regulatory T cell response in a subject; and (c) replacing said putative T cell epitope of said strain of influenza A by exchanging existing amino acid residues found in said T cell epitope with select amino acid residues.

The immediate exemplary embodiment may be further narrowed to include the following: human proteins, human subjects, the Influenza A/Shanghai/2/2013 H7 strain wherein the amino acid residues in the 321$^{st}$ position, the 322$^{nd}$ position and 324$^{th}$ position were exchanged more particularly wherein arginine in the 321$^{st}$ position is exchanged with asparagine, serine in the 322$^{nd}$ position was exchanged with threonine and leucine in the 324$^{th}$ position was exchanged with lysine.

Another embodiment of the present invention is a modified vaccine antigen against a pathogen, wherein said antigen induces T cell memory, B cell memory and antibodies are specific for the protein of said pathogen.

In another aspect of the same embodiment, the modified pathogen is influenza A, influenza B or influenza C, more particularly influenza A and its serotypes H1N1, H2N2, H3N2, H5N1, H7N7, H1N2, H9N2, H7N2, H7N3, H10N7 or H7N9, even more particularly H7N9, and most particularly influenza A/Shanghai/2/2013.

The recent embodiment may also be narrowed so that protein is the H7 protein of influenza A, more particularly serotype H7N9 and most particularly influenza A/Shanghai/2/2013.

BRIEF DESCRIPTION OF FIGURES

FIG. 2 is the complete sequence of the modified H7 Hemagglutinin (SEQ ID NO: 2). The underlined sequence (1) is the modified cluster 321 (SEQ ID NO: 3).

FIG. 3 is the complete sequence of the Influenza A/Shanghai/2/2013 H7 (SEQ ID NO: 4). The underlined sequence (2) is the T cell epitope cluster identified for modification (SEQ ID NO: 5).

FIG. 4 is the EpiMatrix analysis of Influenza A/Shanghai/2/2013 H7 epitope cluster 321 (SEQ ID NO: 5). Results are shown for CPRYVKQRS (SEQ ID NO: 7), PRYVKQRSL (SEQ ID NO: 8), RYVKQRSLL (SEQ ID NO: 9), YVKQRSLLL (SEQ ID NO: 10), VKQRSLLLA (SEQ ID NO 11), KQRSLLLAT (SEQ ID NO 12), QRSLLLATG (SEQ ID NO 13), RSLLLATGM (SEQ ID NO 14), SLLLATGMK (SEQ ID NO 15), LLLATGMKN (SEQ ID NO 16), LLATGMKNV (SEQ ID NO 17), LATGMKNVP (SEQ ID NO 18), ATGMKNVPE (SEQ ID NO 19).

FIG. 6 are modifications (SEQ ID NO: 6) to cluster 321 (SEQ ID NO: 5) of Influenza A/Shanghai/2/2013 H7 (SEQ ID NO: 4) for EpiVax MOD1 H7 Hemagglutinin (SEQ ID NO: 2). Results are shown for CPRYVKQNT (SEQ ID NO: 20), PRYVKQNTL (SEQ ID NO: 21), RYVKQNTLK (SEQ ID NO: 22), YVKQNTLKL (SEQ ID NO: 23), VKQNTLKLA (SEQ ID NO 24), KQNTLKLAT (SEQ ID NO 25), QNTLKLATG (SEQ ID NO 26), NTLKLATGM (SEQ ID NO 27), TLKLATGMK (SEQ ID NO 28), LKLATGMKN (SEQ ID NO 29), KLATGMKNV (SEQ ID NO 30), LATGMKNVP (SEQ ID NO 18), ATGMKNVPE (SEQ ID NO 19).

FIG. 7 is the EpiMatrix analysis of modified_epitope cluster 321 from Influenza A/Shanghai/2/2013 H7 (SEQ ID NO: 3).

Figure 9:
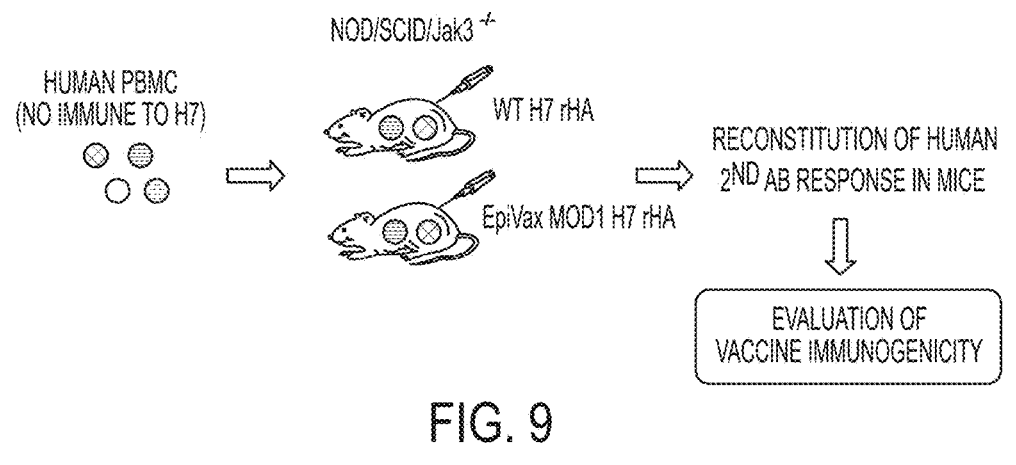

FIG. 9 is a depiction of the mouse model used to test the immunogenicity of the recombinant EpiVax Opt1 H7 Hemagglutinin vaccine.

FIG. 10A depicts peptides representing variants of the immune-dominant and highly conserved HA epitope, from IAV strains other than H7: A(H1N1), A(H3N2) and A(H5N1). FIG. 10B depicts H7H9 ICS peptides ordered by TCR cross-conservation with the human genome. FIG. 10C depicts human analogs of selected H7N9 ICS peptides depicted in FIG. 10B. Each peptide is represented by a diamond. HLA-binding nine-mer frames contained within the source peptide are depicted as squares. For each nine-mer frame, human nine-mers with similar HLA binding affinities and identical TCR-facing residues are shown as triangles and the human proteins from which they are derived are shown as circles.

FIG. 12A is a chart depicting the individual (circles) and average (bars) SI across donors (n=18). The H7N9 peptides are arranged on the chart according to the degree of predicted cross-conservation with peptides from the human genome, as measured by JanusMatrix Delta. FIG. 12B is a graph plotting the average responses to each peptide across 18 healthy donors as measured by SI, negatively correlated with the JanusMatrix Delta, which is a measure of cross-conservation with self.

FIGS. 14A and 14B depict Treg cell expansion induced by Human-like peptides from H7N9. For FIG. 14A, the gating strategy was based on live CD3+ lymphocytes, then analyzed for CD4 vs FoxP3. For FIG. 14B, representative results for a single subject are shown in the dot plots with the averages for three subjects shown in the chart below. *p<0.01.

FIG. 17 depicts an example of an immunogenic influenza HA peptide that contains an EpiBar and the EpiMartix analysis of the promiscuous influenza epitope. The influenza HA peptide scores extremely high for all eight alleles in EpiMatrix and has a cluster score of 22. Cluster scores of 10 are considered significant. The band-like EpiBar pattern is characteristic of promiscuous epitopes. Results are shown for PRYVKQNTL (SEQ ID NO:21), RYVKQNTLK (SEQ ID NO:22), YVKQNTLKL (SEQ ID NO:23), VKQNTLKLA (SEQ ID NO:24) and KQNTLKLAT (SEQ ID NO:25). Z score indicates the potential of a 9-mer frame to bind to a given HLA allele. All scores in the top 5% are considered "hits", while non hits (*) below 10% are masked in FIG. 17 for simplicity.

DETAILED DESCRIPTION

Figure 1:
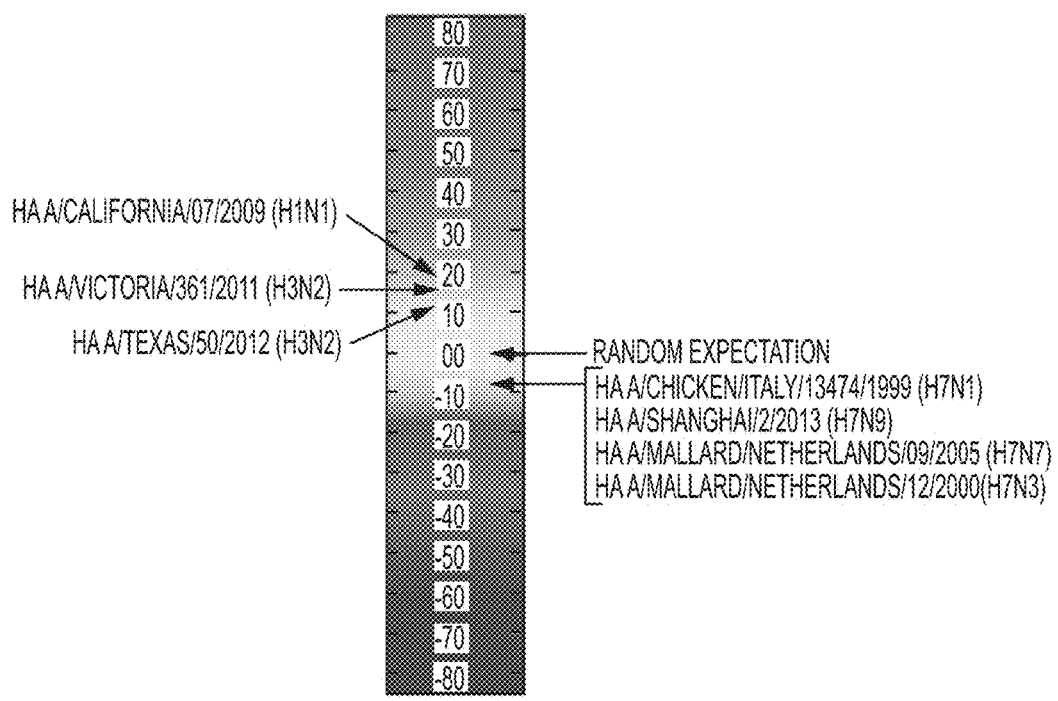
FIG. 1 is the EpiMatrix Immunogenicity scale comparing the potential antigenicity of H7-HA to recent seasonal influenza A strain HA proteins.
Figure 5:
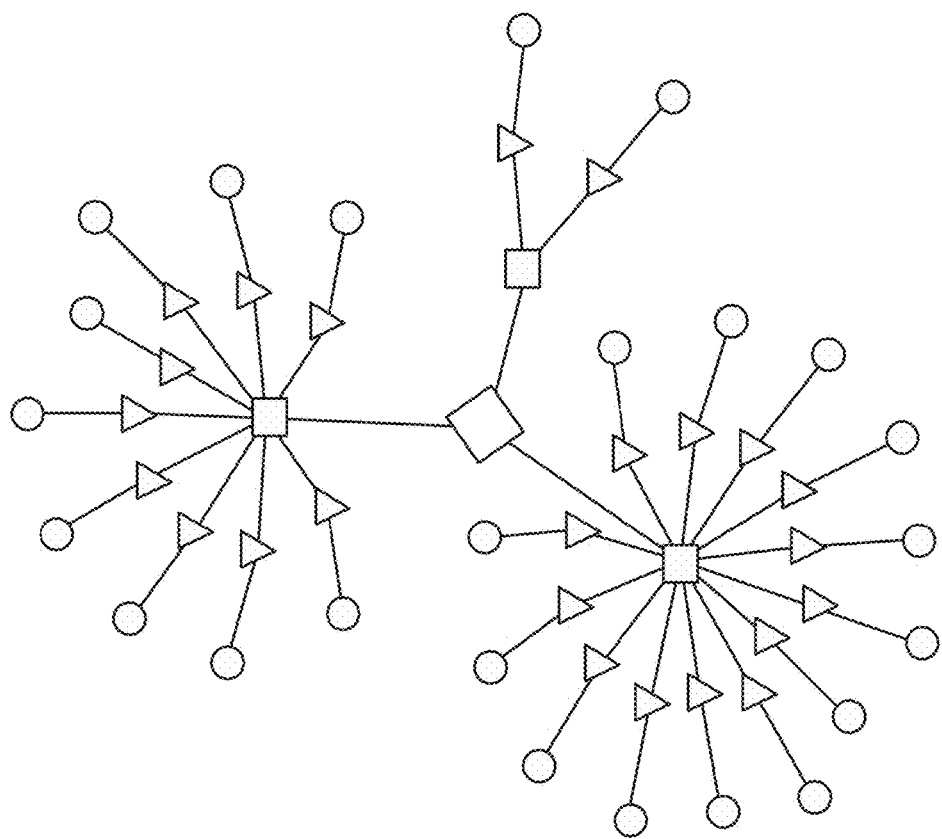
FIG. 5 is the Janus Matrix analysis human epitope network diagram of epitope cluster 321 from Influenza A/Shanghai/2/2013 H7.

Disclosed herein is the modified sequence of the H7 hemagglutinin (FIG. 2). This sequence modification is a 3 amino acid change to the Influenza A/Shanghai/2/2013 H7 cluster 321 (FIG. 6). This cluster was chosen by immunoinformatic analysis for modification because of its predicted T cell epitope content and high predicted cross reactivity to human proteins (FIG. 4 and FIG. 5). The three amino acid change created sequence with notably less human cross conservation (FIG. 6 and FIG. 8) while retaining HLA binding potential (FIG. 7).

Using the EpiMatrix toolkit (EpiVax, Providence, R.I., USA), a comparison of the potential immunogenicity of H7 HA to recent seasonal influenza A strain HA proteins predicted a very low potential immunogenicity for the H7 HA proteins. The analysis also identified key H7N9 HA epitopes that have a high degree of cross-conservation at the T cell receptor (TCR)-facing residues with T cell epitopes in the human genome.

Immunoinformatics was used on the first publicly available (GISAID platform.gisaid.org) sequence of Influenza A/Shanghai/2/2013 H7 (FIG. 3). This analysis identified H7 cluster 321, the underlined sequence (2) of FIG. 3, as a target for modification. The EpiMatrix cluster analysis predicted H7 cluster 321 to be highly conserved across the eight major MHC class II supertypes (FIG. 4). JanusMatrix analysis (EpiVax, Providence, R.I., USA) on cluster 321, predicted that it had high degree of cross-conservation with T cell epitopes in the human genome at T cell receptor-facing residues. The JanusMatrix human epitope network (FIG. 5) shows the epitope, depicted as a square in the center of the starburst where each of the extensions from that symbol represent human protein sequences with cross reactivity to the H7 cluster.

Three sequence changes were made to the A/Shanghai/2/2013 H7 cluster 321 epitope (FIG. 6). These changes introduced a sequence with identity to the influenza Classic H3 epitope CPRYVKQNTLKLAT (SEQ ID NO: 1). As depicted in FIG. 6, amino acid at position 321 (1) was changed from arginine to asparagine; position 322 (2) was changed from serine to threonine; and position 324 (3) was changed from leucine to lysine. The complete modified sequence of H7 Hemagglutinin is provided in FIG. 2, with the modified cluster 321 shown as underlined sequence (1).

EpiMatrix analysis of the modified cluster shows that the three single amino acid modifications to cluster 321 of A/Shanghai/2/2013 H7 do not change the epitope content or conservation of the cluster across the eight major MHC class II supertypes (FIG. 7).

Figure 8:
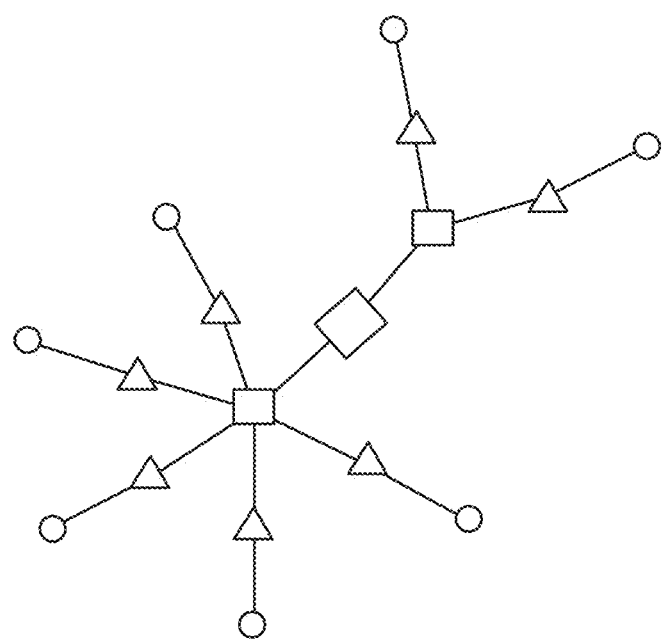
FIG. 8 is the Janus Matrix analysis human epitope network diagram of the modified Influenza A/Shanghai/2/2013 H7 epitope cluster 321.

The three single sequence modifications to cluster 321 of A/Shanghai/2/2013 H7 reduced the cross-conservation with T cell epitopes in the human genome of the T cell receptor-facing residues, as illustrated in the JanusMatrix analysis epitope network diagram in FIG. 8.

Figure 12A:
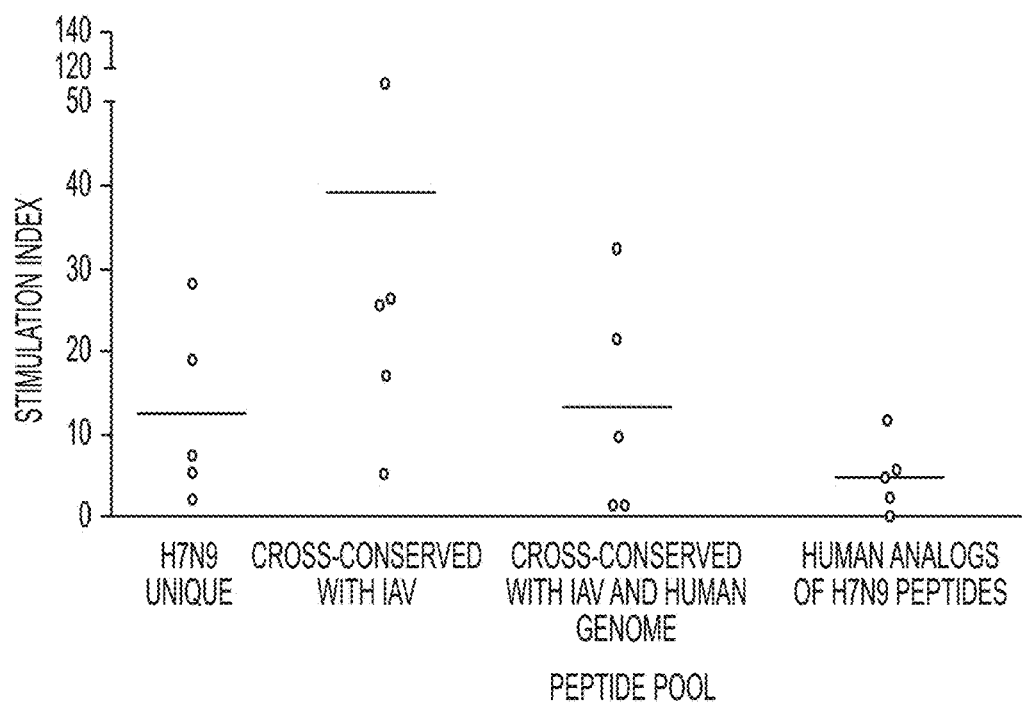
FIGS. 12A and 12B illustrate Human IFNγ responses to individual H7N9 peptides and controls.
Figure 12B:
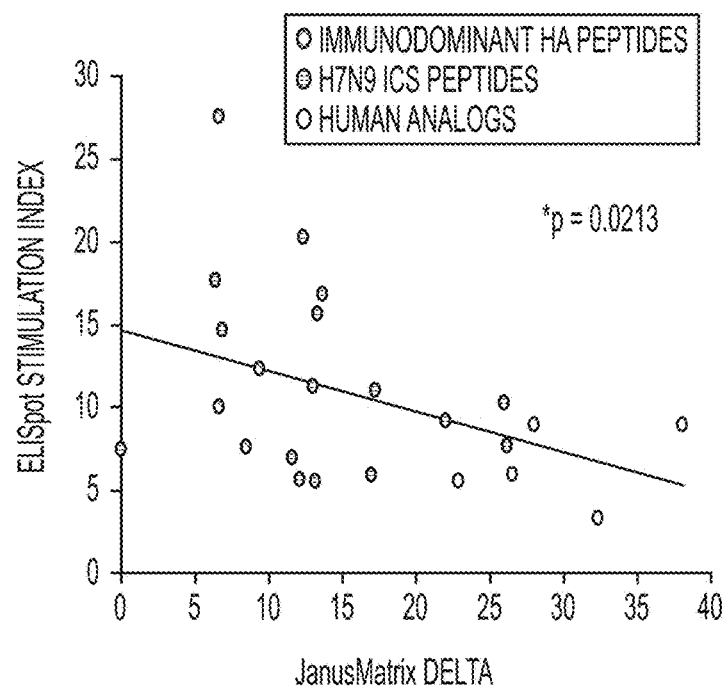

Using the JanusMatrix tool (EpiVax, Providence, R.I., USA), epitopes in H7N9 that are cross-conserved with multiple predicted HLA ligands from human proteins were identified. Based on the discovery of a human-like Treg epitope in HCV (Losikoff P T et al., *J. Hepatol., pii:S0168-8278(14)00613-8, 2014*) similarly cross-conserved epitopes in H7N9 were found to be potentially responsible for the attenuation of adaptive immunity to H7N9. The responses of H7N9-naïve subject PBMCs to H7N9 influenza T cell epitope peptides were evaluated and were found to be inversely correlated with their degree of cross-conservation with the human genome on their TCR face (FIG. 12B).

Figure 15A:
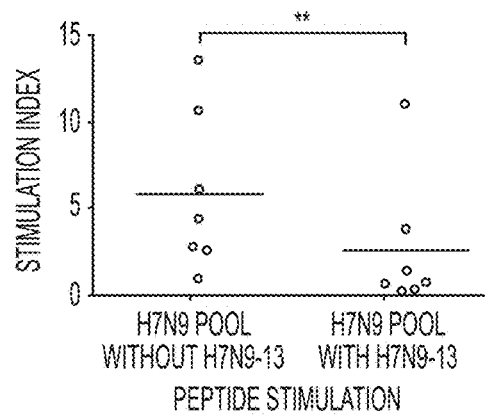
FIGS. 15A-15C are various graphs representing the suppressive activity of the H7 homolog of the seasonal influenza immunodominant HA epitope. Peptide H7N9-13, the H7N9 variant of an immunodominant HA epitope, was associated with a reduction in T cell response when co-administered with other peptides. Healthy donor ELISpot responses to a pool of H7N9 peptides were significantly decreased in the presence of H7N9-13 (n=7) (FIG. 15A), but not H7N9-9, a less human-like peptide (n=4) (FIG. 15B). H7N9-13 was able to suppress responses to other immunodominant HA peptides from circulating IAV strains (n=2) (FIG. 15C). *p<0.05. **p<0.01.
Figure 15B:
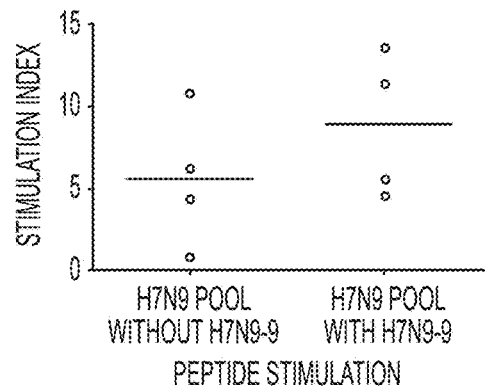
Figure 15C:
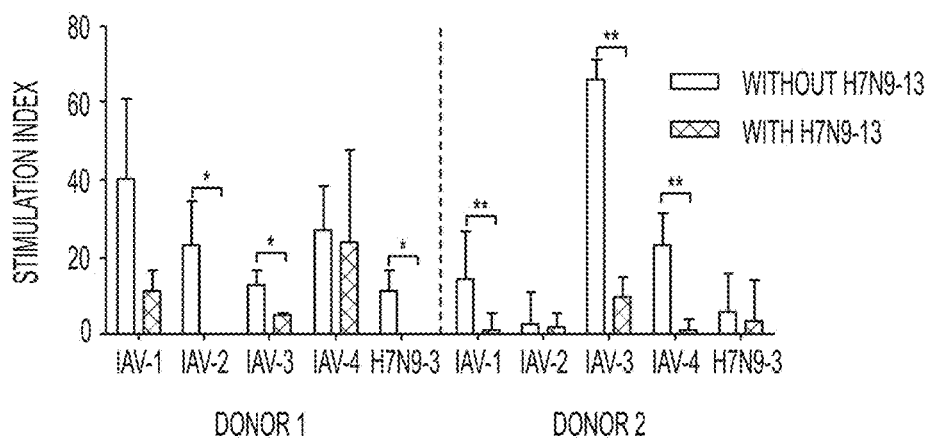

Tregs were discovered to expand in vitro in co-cultures with the human-like H7 epitopes (FIG. 14A and FIG. 14B). The functionality of the expanded Tregs in bystander suppression assays was learned (FIGS. 15A-15C). The exact origin of the Treg cells that respond to the human-like H7N9 epitopes remains to be defined (thymic-derived natural Tregs or induced peripheral Tregs), the implications for vaccine development are clear. In the context of natural infection or un-adjuvanted vaccination using H7N9 HA, Treg responses are induced by these epitopes, and humoral immune responses may be diminished and delayed, as has been reported in H7N9 infection (Guo L et al., *Emerg. Infect. Dis.*, 20:192-200, 2013).

Using JanusMatrix, at the level of the TCR-HLA-II-peptide interaction, there is evidence to support the designation of amino acids in positions 2, 3, 5, 7, and 8 as 'TCR-facing' used to identify homologous epitopes in sets of peptides predicted to be restricted by the same HLA. There is also a role for several positions in the class II HLA ligand that lie outside of the central binding groove, notably at the N-terminus.

JanusMatrix was used to compare 'analogs' to human-origin peptides that were cross-conserved with selected H7N9 ICS peptides without evaluating the influence of TCR cross-conservation with epitopes derived from other human pathogens or from human commensals. Evidence for immune modulation (termed 'heterologous immunity') in a range of viral infections is known, focusing on class I HLA-restricted epitopes. Epitopes that are cross-conserved with the human microbiome have also been described, and may contribute to T cell reactivity (Su L F et al., *Immunity*, 38:373-83, 2013).

The ratio of human genome to human microbiome cross-conservation associated with a regulatory, rather than effector, T cell response has been reported (Moise L et al., *Hum. Vaccin. Immunother.*, 9:1577-86, 2013). The JanusMatrix Delta score, which significantly correlated with the magnitude of effector T cell response (FIG. 12B) was used.

T cell responses in re-stimulation assays using PBMC from unexposed donors were analyzed. The in vitro studies of naïve donors were determined to be relevant since the responses observed may be representative of responses that might be generated following vaccination or infection of H7N9-unexposed human subjects.

H7N9 influenza T cell epitopes that have a high degree of cross-conservation with the human host can expand Tregs in vitro and reduce IFNγ secretion in PBMC when co-incubated with other H7N9 peptides in contrast to epitopes that are less cross-conserved with self (FIG. 14A, FIG. 14B, and FIGS. 15A-15C). Cross-conservation of T helper epitopes with epitope sequences in the human proteome is an important modulator of immune response to viral pathogens.

Modulation of T and B cell responses by the claimed human-like epitopes reduces the titer and affinity of neutralizing antibodies to H7N9 HA, in vaccination and infection. In addition to posing a barrier to the success of conventional approaches currently being used to develop H7N9 vaccines, 'immune camouflage' can be added to the list of mechanisms by which human pathogens may escape from or modulate human immune defense.

The potential immunogenicity of H7N9 was evaluated using EpiMatrix (EpiVax, Providence, R.I., USA). Several H7N9 CD4+ T cell epitopes that were more cross-conserved with human sequences than were similar epitopes found in other influenza strains were identified (FIG. 10). An H7 HA sequence that corresponds in sequence location to the immunodominant epitope of A(H3N2) and A(H1N1) bears mutations at TCR-facing positions that increase its resemblance to self-antigens in the context of HLA-DR presentation. The human-like H7N9 epitopes were predicted to reduce the H7N9 vaccine efficacy and contribute to lower titer, lower affinity antibody development. In vitro T cell assays were performed using peripheral blood mononuclear cells (PBMC) from naïve human donors, examining the phenotype and function of cells responding to H7N9 class II-restricted T cell epitopes that are cross-conserved with the human genome and compared responses to these peptides with responses to corresponding peptides derived from human proteins and to less cross-conserved peptides in H7N9. Highly cross-conserved epitopes contained in H7N9 protein sequences exhibited low immunogenicity and stimulated functional Tregs, a finding that has significant implications for H7N9 vaccines and viral immunopathogenesis (FIG. 12A, FIG. 12B, FIG. 13, FIG. 14A, FIG. 14B, and FIGS. 15A-15C).

Definitions

The term "adjuvant," as used herein, refers to a substance that helps and enhances the effect of a vaccine.

The term "amino acid sequence," as used herein, refers to the order in which amino acids join to form peptide chains, i.e., linked together by peptide bonds.

The term "antibody" (also known as an "immunoglobulin"), as used herein, refers to a protein that is produced by plasma cells and used by the immune system to identify and neutralize foreign objects such as viruses.

The term "antibodies raised," as used herein, refers to those antibodies that are produced by the plasma cells of the subject who has been infected with a pathogen or vaccinated.

The term "antigen," as used herein, refers to a substance that the immune system perceives as being foreign or dangerous.

The term, "clade," as used herein, refers to a life-form group consisting of an ancestor and all its descendants.

The term "effector T cell(s)," as used herein, refers to one or more lymphocyte (as a T cell) that has been induced to differentiate into a form (as a cytotoxic T cell) capable of mounting a specific immune response, also called an effector lymphocyte.

The term "homology" (or "homologies"), as used herein, refers to a similarity in sequence of a protein or nucleic acid between organisms of the same or different species.

The term "human microbiome," as used herein, refers to the aggregate of microorganisms capable of living inside or on the human body.

The term "human proteome," as used herein, refers to the entire f proteins expressed by a human genome, cell, tissue or organism at a certain time. More specifically, it is the set of expressed human proteins in a given type of cell or organism, at a given time, under defined conditions.

The term "induces a response" (or "induces responses"), as used herein, refers to an entity's ability to cause another entity to function.

The term "cDNA," as used herein, refers to "complementary DNA" which is synthetic DNA transcribed from a specific RNA through the reaction of the enzyme reverse transcriptase.

The terms "transfect" or "transfecting" or "transfection," as collectively used herein, refer to the process of deliberately introducing nucleic acids into a target cell.

The term "vector," as used herein, refers to a vehicle used to transfer genetic material to a target cell and the "cloning site" is that portion of the vector which is able to make copies of DNA fragments.

The term "Opt_1," as used herein, refers to a purposefully, modified version.

The term "WT," as used herein, refers to the "wild type" version or a version that found in nature.

Influenza virus, as used herein, refers to a family of RNA viruses that includes six genera: Influenza virus A, Influenza virus B, Influenza virus C, Isavirus, Thogotovirus and Quaranjavirus. The first three genera contain viruses that cause influenza in vertebrates, including birds (see also avian influenza), humans, and other mammals Isaviruses infect salmon; thogotoviruses infect vertebrates and invertebrates, such as ticks and mosquitoes. The three genera of Influenza virus, which are identified by antigenic differences in their nucleoprotein and matrix protein, infect vertebrates as follows: Influenza virus A infects humans, other mammals, and birds, and causes all flu pandemics; Influenza virus B infects humans and seals; and Influenza virus C infects humans, pigs and dogs.

The term, "memory B cell(s)," as used herein, refers to one or more B cell sub-type formed within germinal centers following primary infection important in generating an accelerated and more robust antibody-mediated immune response in the case of re-infection (also known as a secondary immmune response).

The term "memory T cells," as used herein, refers to a subset of infection, as well as potentially infection-fighting T cells (also known as a T lymphocyte), that have previously encountered and responded to their cognate antigen.

The term "natural infection," as used herein, refers to the invasion and multiplication of microorganisms such as bacteria, viruses, and parasites that are not normally present within the body. An infection may cause no symptoms and be subclinical, or it may cause symptoms and be clinically apparent. An infection may remain localized, or it may spread through the blood or lymphatic vessels to become systemic (bodywide). The invading microrganisms are not introduced intentionally into the host, i.e., by injection, but enter as the result of natural bodily functions such as breathing or eating, via normal areas of exposure such as eyes, ear canals, mouth, nasal cavity and lungs, urethra, anus and the like or open wounds such as cuts, scratches or other abrasions.

The term "nucleic acid," as used herein, refers to a complex organic substance present in living cells, especially DNA or RNA, whose molecules consist of many nucleotides linked in a long chain.

The term "pathogen," as used herein, refers to a bacterium, virus, or other microorganism that can cause disease.

The term "polypeptide," as used herein, refers to a linear organic polymer consisting of a large number of amino-acid residues bonded together in a chain, forming part of (or the whole of) a protein molecule.

The term "position," as used herein when referring to amino acid sequences, refers to the place that a particular amino acid residue may be found in a sequence of amino acids. For instance, stating that an amino acid is in the first position of a polypeptide indicates that it is the originating amino acid is located at the N-terminal of said polypeptide.

The term "raised against," as used herein when discussing vaccines, refers to those antibodies that are produced by the plasma cells of the subject who has been infected with a pathogen or vaccinated with antigen.

The term "regulatory T cells (also referred to as "Tregs" and formerly known as 'suppressor T cells')," as used herein, refers to a subpopulation of T cells which modulate the immune system, maintain tolerance to self-antigens, and abrogate autoimmune disease. These cells generally suppress or down-regulate induction and proliferation of effector T cells.

The term "select amino acid residues," as used herein, refers to amino acids carefully chosen by the inventors for certain properties and physiochemical attributes said amino acids possess so as to replace certain amino acid residues in a given polypeptide.

The term "serotype," as used herein, refers to distinct variations within a species of bacteria or viruses.

The term "strain," as used herein, refers to a genetic subtype of a micro-organism (e.g., virus or bacterium or fungus).

The term "T cell epitope (also known as antigenic determinant)," as used herein, refers to part of an antigen that is recognized by the immune system, specifically by T cells.

The term, "vaccination," as used herein, refers to the administration of antigenic material to stimulate an individual's immune system to develop adaptive immunity to a pathogen.

The term "vaccine," as used herein, refers to a substance used to stimulate the production of memory T cells and antibodies and provide immunity against one or several diseases, prepared from the causative agent of a disease, its products, or a synthetic substitute, treated to act as an antigen without inducing the disease.

The term "variant," as used herein, refers to a form or version of something that differs in some respect from other forms of the same thing or from a standard.

The term "wild type," as used herein, refers to the phenotype of the typical form of a species as it occurs in nature.

Abbreviations used herein are defined as follows:
APC antigen presenting cell
CEFT Cyto-megalovirus (HCMV), Epstein-Barr virus, Flu viruses, Tetanus toxoid virus
DMSO dimethyl sulfoxide
DPBS Dulbecco's Phosphate-Buffered Saline
HBSS Hank's Balanced Salt Solution
HLA human leukocyte antigen
HPLC high performance liquid chromatography
IAV influenza A viruses
ICS immunogenic consensus sequences
MHC major histocompatibility complex
PBMC peripheral blood mononuclear cells
PHA phytohaemagglutinin
TCR T cell receptor
Tregs T regulatory cells
TRF time resolved fluorescence The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B and C as components.

In Silico Analysis of A/Shanghai/2/2013 H7

The amino acid sequence of H7N9 influenza for both overall and regional immunogenic potentials was analyzed using the EpiMatrix System (EpiVax, Providence, R.I., USA). Identified putative epitope clusters were further screened against the non-redundant protein databases available from GenBank® (National Institutes of Health, Bethesda, Md., USA) the immune epitope database at the La Jolla Institute for Allergy and Immunology (La Jolla, Calif., USA), and the database of known MHC ligands and T cell epitopes maintained by EpiVax, Inc. (EpiVax, Providence, R.I., USA).

Evaluation of Overall Immunogenicity—Class II of A/Shanghai/2/2013 H7

Input sequences were parsed into overlapping 9-mer frames and each frame was evaluated with respect to a panel of eight common Class II alleles, i.e., "super-types", functionally equivalent to, or nearly equivalent to, many additional "family member" alleles. The eight super-type alleles, along with their respective family members, "cover" well over 98% of the human population (Southwood, S et al., *J. Immunol.*, 160(7):3363-73, 1998). Each frame-by-allele "assessment" predicted HLA binding affinity. The EpiMatrix System assessment scores ranged from approximately −3 to +3 and were normally distributed. The EpiMatrix System assessment scores above 1.64 were classified as "hits"; indicating potential immunogenicity, with a significant chance of binding to HLA molecules with moderate to high affinity and, therefore, having a significant chance of being presented on the surface of APCs such as dendritic cells or macrophages where they may be interrogated by passing T cells.

The more HLA ligands (i.e., EpiMatrix hits) contained in a given protein, the more likely that protein induces an immune response. A score was given to each protein referred to as The EpiMatrix Protein Score which was the difference between the number of predicted T cell epitopes expected for a protein of a given size and the number of putative epitopes predicted by the EpiMatrix System. The EpiMatrix Protein Score is correlated with observed immunogenicity. The EpiMatrix Protein Scores were "normalized" and plotted on a standardized scale. The EpiMatrix Protein Score of an "average" protein is zero and scores above zero indicate the presence of excess MHC ligands and denote a higher potential for immunogenicity while scores below zero indicate the presence of fewer potential MHC ligands than expected and a lower potential for immunogenicity. Proteins scoring above +20 are considered to have a significant immunogenic potential.

Evaluation of Regional Immunogenicity—Class II of A/Shanghai/2/2013 H7

For Class II, potential T cell epitopes are not randomly distributed throughout protein sequences but instead tend to "cluster" in specific regions. T cell epitope "clusters" range from nine to roughly twenty-five amino acids in length and, considering their affinity to multiple alleles and across multiple frames, can contain anywhere from four to forty binding motifs. It was discovered that many of the most reactive T cell epitope clusters contain a single 9-mer frame which is predicted to be reactive to at least four different HLA alleles (hereinafter referred to as an "EpiBar"). Sequences that contain EpiBars include Influenza Hemagglutinin 306-318 (Cluster score of 22), Tetanus Toxin 825-850 (Cluster score of 46), and GAD65 557-567 (Cluster score of 23). A visual representation of an EpiBar is shown in FIG. 17, which depicts an example of an EpiBar and the EpiMatrix analysis of a promiscuous influenza epitope. Consider the influenza HA peptide, an epitope known to be promiscuously immunogenic. It scores extremely high for all eight alleles in EpiMatrix. As stated above, its cluster score is 22. Cluster scores higher than 10 are considered to be significant. The band-like EpiBar pattern is characteristic of promiscuous epitopes. Results are shown in FIG. 17 for PRYVKQNTL (SEQ ID NO: 21), RYVKQNTLK (SEQ ID NO: 22), YVKQNTLKL (SEQ ID NO: 23), VKQNTLKLA (SEQ ID NO 24), and KQNTLKLAT (SEQ ID NO 25). Z score indicates the potential of a 9-mer frame to bind to a given HLA allele. All scores in the top 5% are considered "hits", while non hits (*) below 10% are masked in FIG. 17 for simplicity.

It was found that T cell epitope clusters, especially sequences that contain "EpiBars," bind very well to a range of HLA Class II molecules and tend to be very immunogenic in assays of blood samples drawn from human subjects. As reported by McMurry J A et al. (*Vaccine*, 25(16):3179-91, 22/01/2007), nearly 100% of subjects exposed to either Tularemia or Vaccinia through natural infection generated ex vivo T cell response to pools of T cell epitope clusters containing approximately 20 peptides each. It was observed that EpiBars and T cell epitope clusters are very powerful immunogens. The presence of one or more dominant T cell epitope clusters enabled significant immune response to even otherwise low scoring proteins.

In order to find potential T cell epitope clusters, the EpiMatrix analysis results were screened for regions with unusually high densities of putative T cell epitopes. The significant EpiMatrix scores contained within these regions were then aggregated to create an EpiMatrix Cluster Immunogenicity Score, wherein positive scores indicate increased immunogenic potential and negative scores indicate a decreased potential relative to a randomly generated or "average" sequence. T cell epitope clusters scoring above+ 10 were considered to have a significant immunogenic potential.

Figure 18:
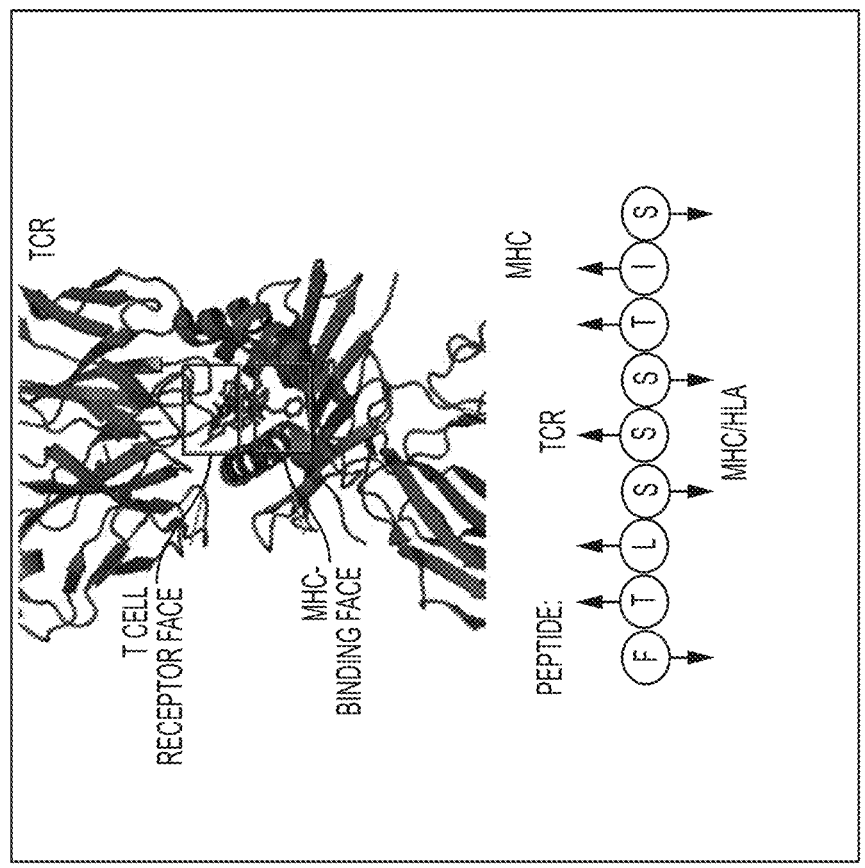
FIG. 18 depicts how the JanusMatrix algorithm considered the amino acid content (SEQ ID NO: 55) of both the MHC facing agretope and the TCR facing epitope. As depicted, each MHC ligand has two faces: the MHC-biding face (agretope, amino acid residues with arrow pointing down towards MHC/HLA), and the TCR-interacting face (epitope, amino acid residues with arrow pointing up towards TCR).

The JanusMatrix algorithm considered the amino acid content (SEQ ID NO: 55) of both the MHC facing agretope and the TCR facing epitope, as shown in FIG. 18. As depicted in FIG. 18, each MHC ligand has two faces: the MHC-biding face (agretope, amino acid residues with arrow pointing down towards MHC/HLA), and the TCR-interacting face (epitope, amino acid residues with arrow pointing up towards TCR). Predicted ligands with identical epitopes and variant agretopes may stimulate cross reactive T cell responses, providing they bind to the same MHC allele. Input sequences were parsed into overlapping 9-mer frames and screened against a chosen reference database. Reference sequences with compatible agretope (i.e., predicted by EpiMatrix to bind the same HLA as the input peptide) and exactly matching the TCR contacts of the input peptide were returned.

Results

The in silico analysis performed identified the presence of a significant T cell epitope at the $324^{th}$ position of the A/Shanghai/2/2013 H7 strain of influenza A ('epitope 321'). The results are reported in FIG. 4. In addition, correspondence between the TCR contacts of epitope 321 and T cell epitopes resident within the human genome was established. See FIG. 5. The EpiMatrix analysis of modified_epitope cluster 321 from Influenza A/Shanghai/2/2013 H7 is shown in FIG. 7. The in silico analysis performed also discovered a lack of significant correspondence between the TCR contacts of the common variant and T cell epitopes contained within the human genome. See FIG. 8. The proposed modifications of the A/Shanghai/2/2013 H7 strain of influenza is depicted by FIG. 6. FIG. 2 is the sequence for the A/Shanghai/2/2013 H7 variant conceived, constructed and tested and claimed in the immediate application.

Genome Analysis and Epitope Prediction

Four human H7N9 influenza sequences (A/Hangzhou/1/2013, A/Anhui/1/2013, A/Shanghai/1/2013, and A/Shanghai/2/2013) from GISAID (platform.gisaid.org) were analyzed for HLA class II-restricted epitopes, and constructed immunogenic consensus sequences (ICS) were constructed to enable broad HLA and strain coverage. Fifteen representative ICS with varying degrees of cross-conservation with self were selected in addition to four publicly-available influenza A epitopes from A(H1N1), A(H3N2), and A(H5N1) and five peptides from human proteins to serve as positive controls and human 'analogs' of the H7N9 peptides, respectively. The human analog peptides were among those identified by JanusMatrix (EpiVax, Providence, R.I., USA) as likely targets of mimicry by selected H7N9 peptides.

Peptide Similarity to Circulating IAV and Cross-Conservation with Human Genome

The similarity of H7N9 peptides to other IAV strains has been reported (De Groot A S et al., *Hum. Vaccin. Immunother.*, 9:950-6, 2013). Cross-conservation with the human genome was evaluated using JanusMatrix (EpiVax, Providence, R.I., USA). The UniProt reviewed human genome database was translated as the source of human sequences for comparison (The UniProt Consortium, *Nucleic Acids Res.*, 40:D71-5, 2012).

H7N9 ICS peptides were generated as described by De Groot A S et al. (*Hum. Vaccin. Immunother.*, 9:950-6, 2013). Given a peptide containing multiple HLA-binding nine-mer frames, JanusMatrix divided each such frame into T cell receptor-facing residues (positions 2, 3, 5, 7, and 8) and HLA-binding residues (positions 1, 4, 6, and 9). Subsequently, JanusMatrix searched for potentially cross-conserved epitopes (100% TCR-facing identity and predicted to bind at least one of the same HLA supertypes) in the human genome database. A quantitative measure of human genome cross-conservation called 'JanusMatrix Delta' score was calculated by applying a user-defined deduction to each EpiMatrix hit in the source peptide for each TCR-matched nine-mer found in the human genome (set for the purpose of the current study at 10% of the human nine-mer's Z-score). A higher JanusMatrix Delta indicates a greater number of TCR matches with autologous (human) peptides which themselves share HLA restrictions with the query peptide. JanusMatrix Delta values for the peptides ranged from 0 to 37.89. After deduction, the hits in the source peptide were summed and used to calculate a JanusMatrix-adjusted Cluster Score. The difference between a peptide's original EpiMatrix Cluster Score and its JanusMatrix-adjusted Cluster Score was calculated (hereinafter referred to as the "JanusMatrix Delta"), i.e., JanusMatrix Delta=EpiMatrix Cluster Score−JanusMatrix-adjusted Cluster Score.

A higher JanusMatrix Delta value indicated that the original potential for immunogenicity was discounted by greater cross-conservation with the human genome.

A complete list of peptides, along with their sequence similarity to corresponding peptides in circulating IAV strains and cross-conservation with the human genome, is provided in Table 1.

TABLE 1

Selected ICS Peptides from H7N9 Influenza And Controls from Circulating IAV Strains or Human Proteins

| Peptide Description | Peptide Name | Peptide Sequence | SEQ ID NO | Source Protein | % Similiarity with IAV | | Cross-convservation with Human Sequences | |
|---|---|---|---|---|---|---|---|---|
| | | | | | A/California/ 7/2009(H1N1) | A/Victoria/ 361/2011(H3N2) | Janusmatrix Delta | # of Matches |
| Immunodominant HA peptides from circulating iAV strains | IAV-1 | PKYVKSTKLRLATG | 31 | HA | 100% | 85% | 6.70 | 10 |
| | IAV-2 | PRYVKQSTLKLATG | 32 | HA | 85% | 100% | 8.45 | 13 |
| | IAV-3 | PRYVKQNTLKLATG | 33 | HA | — | 97% | 6.57 | 7 |
| | IAV-4 | PKYVKSNRLVLATG | 34 | HA | 89% | — | 9.37 | 11 |
| H7H9 ICS peptide | H7H9-1 | RIDFHWLMLNPNDTVTFS | 35 | HA | — | — | 0.00 | 0 |
| | H7H9-2[a] | YAEMKWLLSNTDNAAFPQ | 36 | HA | — | — | 6.37 | 8 |
| | H7H9-3 | KGILGFVFTLTVPSERGLQ | 37 | M1 | 100% | 100% | 6.77 | 10 |
| | H7H9-4 | QPEWFRNVLSIAPIMFSNK | 38 | PB1 | 97% | 99% | 11.50 | 14 |
| | H7H9-5 | GFTKRTSGSSVKRE | 39 | PB2 | 93% | 93% | 12.05 | 17 |
| | H7H9-6 | RRDQKSLRGRSSTLGLDI | 40 | NS1 | 94% | 94% | 12.33 | 15 |
| | H7H9-7 | NYLLTINKQVLAELQDIE | 41 | PA | 96% | 97% | 13.00 | 14 |
| | H7H9-8 | DKLYERVKRQLRENAEED | 42 | HA | - | 83% | 13.22 | 24 |
| | H7H9-9 | AVKLYKKLKREMTFHGA | 43 | M1 | 97% | 95% | 13.68 | 35 |
| | H7H9-10 | AANIIGILHLILWILDRL | 44 | M2 | 96% | 100% | 15.36 | 16 |
| | H7H9-11 | SRKLLLIVQALRDNLEPG | 45 | PA | 100% | 98% | 16.99 | 51 |
| | H7H9-12 | QITFMQALQLLLEVE | 46 | NEP | 100% | 93% | 17.22 | 18 |
| | H7H9-13 | PRYVKQRSLLLATG | 47 | HA | — | 89% | 21.85 | 24 |
| | H7H9-14A[b] | IVYWKQWLSLKNLTQ | 48 | PB1-F2 | — | — | 25.87 | 24 |
| | H7h9-14B[b] | WKQWLSLKNTLTQGSL | 49 | PB1-F2 | — | — | 26.05 | 25 |
| Autologous peptides sharing identical TCR contact residues with selected H7H9 ICS peptides | 5-HUMAN-A | LSGLKRASASSLRSI | 50 | RhoGTPase-activating protein 42 | — | — | 27.97 | 36 |
| | 5-HUMAN-B | RGILKRNSSSSSTDS | 51 | Synaptotagmin-like protein 2 | — | — | 37.89 | 38 |
| | 12-HUMAN | VRHFMQSLALLMSPV | 52 | Ectopic p granules protein 5 homolog | — | — | 22.71 | 14 |
| | 14A-HUMAN | EEDLKQLLALKGSSY | 53 | Mitochondrial NAD kinase 2 | — | — | 32.21 | 46 |
| | 14B-HUMAN | NLELLSLKRLTLTTS | 54 | Hyccin | — | — | 26.76 | 51 |

[a]Similar to avian H7.
[b]Similar to TIV and LIAV backbone strains.

Column 1: groups assigned to peptides based on their immunological characteristics.

Column 2: peptide names. H7N9 ICS peptide names are ordered by JanusMatrix Delta.

Human analog peptides are numbered according to their corresponding H7N9 peptide.

Column 3: peptide sequence.

Column 4: source protein of each peptide, either from IAV or the human proteome.

Column 5: percentage of similarity with IAV. Similarity to circulating strains of IAV was determined by comparing each peptide to its corresponding sequence in either of the two IAV strains from the 2012/13 TIV. There was no conservation with Influenza B strain Wisconsin/1/2010 for any peptide. Any percentage that was lower than 80% was represented by '-'.

Column 6: cross-conservation of each peptide with the human genome represented by JanusMatrix Delta and the number of matches found in the human database.

Grouping Peptides by Predicted Immunological Properties

Figure 10A:
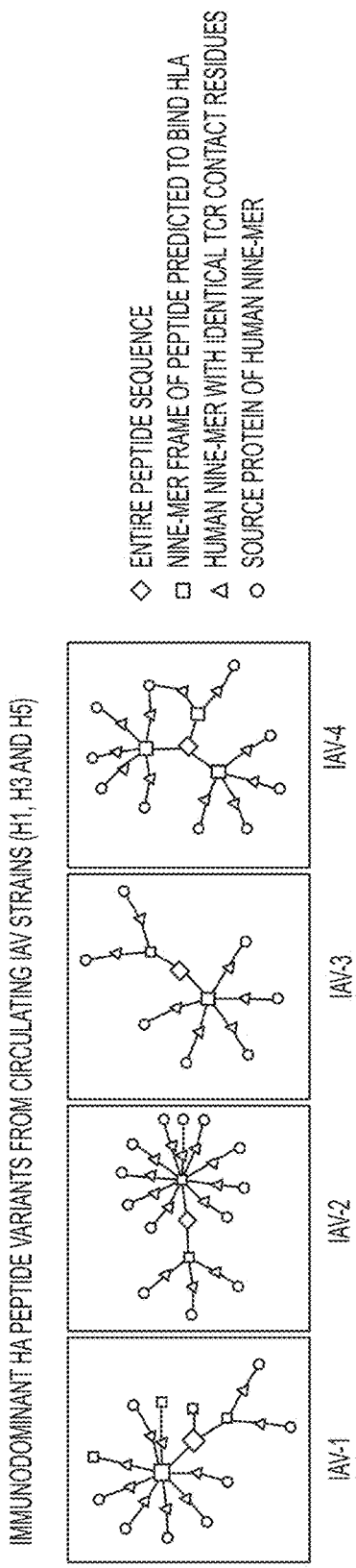
FIGS. 10A-10C depicts different categories of peptides analyzed in JanusMatrix for human sequence cross-conservation with the human genome, visualized in Cytoscape networks.
Figure 10B:
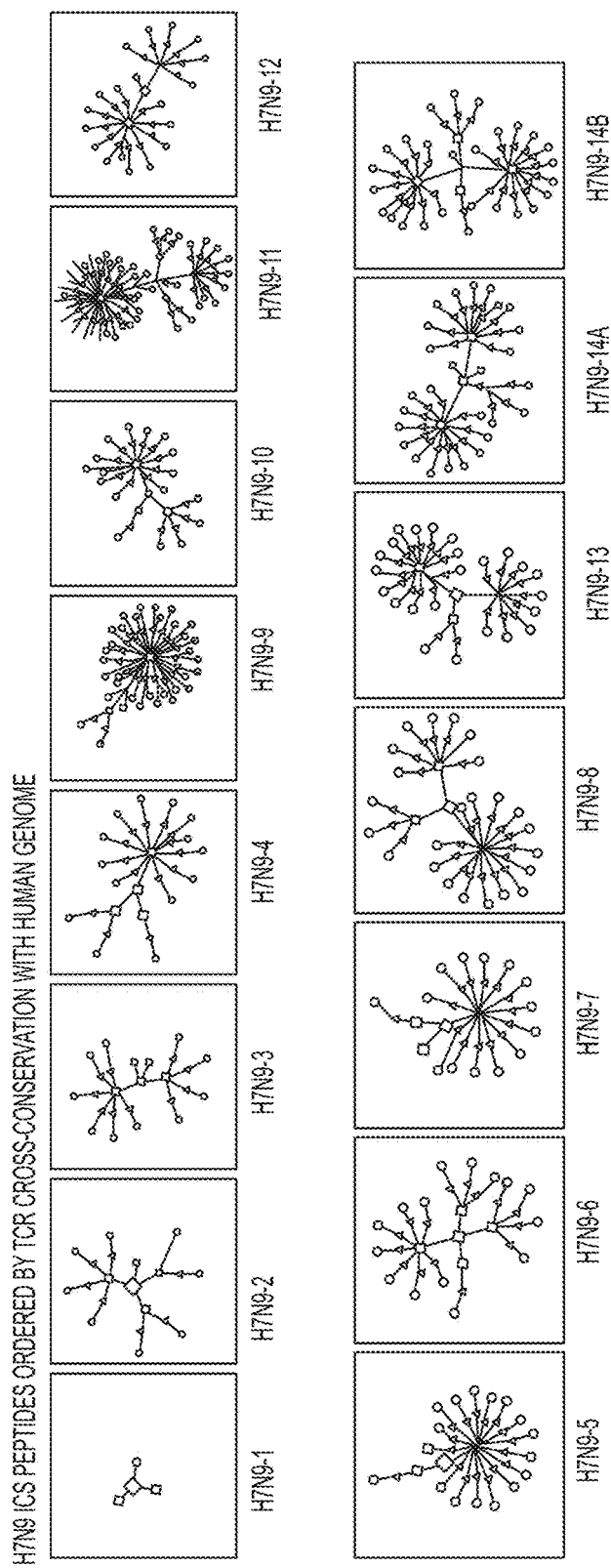
Figure 10C:
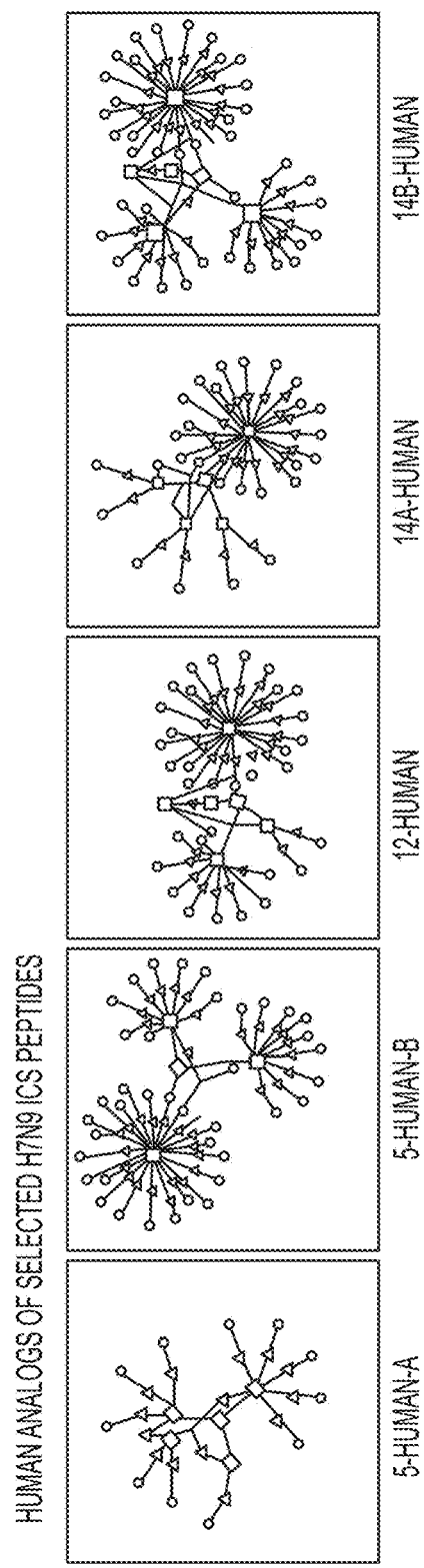
Figure 11:
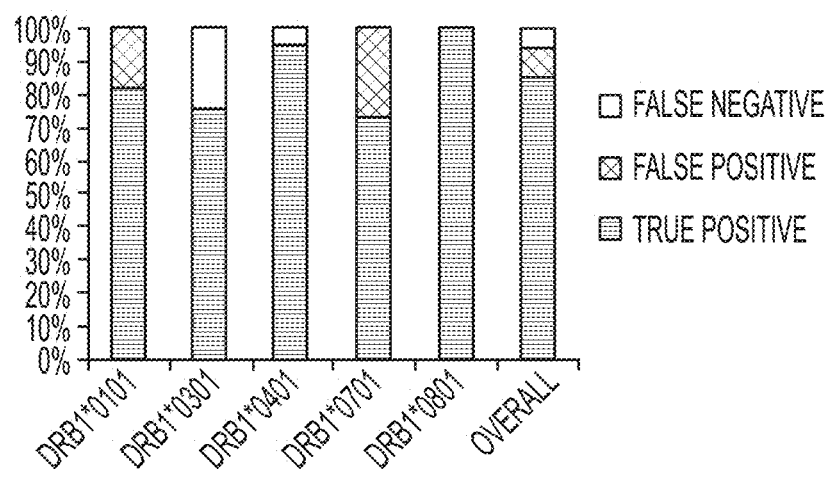
FIG. 11 compares immunoinformatic predictions and HLA binding in vitro. The HLA class II binding result for each peptide was compared to its EpiMatrix Z-score for the corresponding HLA allele. True positive (black) bars reflect correctly predicted HLA-binding peptide results. False positive (gray) bars reflect incorrectly predicted HLA-binding peptide results. False negative (white) bars reflected incorrectly predicted non-binding peptide results.

Cytoscape (Cytoscape Consortium, San Diego, Calif., USA) was used to provide a qualitative analysis of the predicted cross-reactivity between each peptide and the human genome. FIGS. 10A-10C shows Cytoscape networks for each of the peptides.

To compare immune responses to IAV epitopes in vitro using human PBMC, IAV peptides that could elicit several types of possible immune responses were selected. The first group consisted of peptides representing variants of the immune-dominant and highly conserved HA epitope, from IAV strains other than H7: A(H1N1), A(H3N2) and A(H5N1).

The second group of peptides, depicted in FIG. 10B, was selected from a list of ICS peptides derived from the H7N9 antigens (H7N9 ICS peptides) (De Groot A S et al., *Hum. Vaccin. Immunother.,* 9:950-6, 2013). A subset of the 101 ICS generated by the EpiAssembler algorithm (EpiVax, Providence, R.I., USA) were selected for this study on the basis of maximal promiscuous HLA binding potential, lack of cysteines and hydrophobic domains known to result in difficulties with peptide synthesis, and predicted TCR/HLA matches with the human genome using the JanusMatrix algorithm described above. The H7N9 ICS peptides are ordered by their JanusMatrix Delta scores. In some of the assays described, this set of peptides was further separated into pools according to their degree of cross-conservation with the human genome.

For those H7N9 peptides with the most extensive human cross-conservation, one or two peptides from human sequences with which the corresponding H7N9 peptide shared TCR-facing residues were selected for synthesis, as depicted in FIG. 10C. These human 'analog' peptides were numbered by the H7N9 peptide with which they share TCR-facing amino acids. For example, 12-HUMAN is the human analog of peptide H7N9-12.

Peptide Synthesis

The peptides of the present invention were prepared in a variety of ways using commercially available starting materials, compounds known in the literature, or from readily prepared intermediates, by employing standard synthetic methods and procedures either known to those skilled in the art. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B. and March, *J., March's Advanced Organic Chemistry: Reactions, Mechanisms, and Structure,* 5$^{th}$ edition, John Wiley & Sons: New York, 2001; Greene, T. W., Wuts, P.G.M., *Protective Groups in Organic Synthesis,* 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L Paquette, ed., *Encyclopedia of Reagents for Organic Synthesis*, John Wiley and Sons (1995), incorporated by reference herein, are useful and recognized reference textbooks of organic synthesis known to those in the art.

Synthetic peptides were manufactured using 9-fluoronylmethoxycarbonyl (Fmoc) chemistry by 21$^{st}$ Century Biochemicals (Marlboro, Mass., USA). Approximately, 20.1 mg of peptide was produced with a peptide purity was >80% as ascertained by analytical reversed phase HPLC. Peptide mass was confirmed by tandem mass spectrometry. The prepared peptides had the appearance of a white powder.

Class II HLA Binding Assay

HLA class II binding affinity assays were performed to validate the computational predictions. All 24 peptides were evaluated for binding affinity in competition assays for five common HLA DRB1 alleles: HLA DRB1*0101, DRB1*0301, DRB1*0401, DRB1*0701, and DRB1*0801 (FIG. 11). Non-biotinylated test peptides over three concentrations (1, 10, and 100 μM) were used to compete for binding against a biotinylated standard peptide (25 nM) to soluble class II molecules (Benaroya Institute, Seattle, Wash., USA). The reaction was incubated at 37° C. for 24 hours to reach equilibrium. Class II HLA-peptide complexes were then captured on 96-well plates coated with pan anti-HLA-DR antibodies, e.g., L243, anti-HLA-DRA (BioXCell, West Lebanon, N.H., USA). The micro-well plates were then washed to remove excess peptide and incubated with Europium-labeled streptavidin (Perkin-Elmer, Hopkinton, Mass., USA) for one hour at room temperature. Europium activation buffer (Perkin-Elmer, Hopkinton, Mass., USA) was added to develop the plates for 15-20 minutes at room temperature before the plates were read on a Time Resolved Fluorescence (TRF) plate reader (BMG Labtech GMBH, Ortenberg, Del.). Assays were performed in triplicate. Binding assays were performed for all 24 peptides, for five alleles: DRB1*0101, DRB1*0301, DRB1*0401, DRB1*0701, and DRB1*0801, a selection of HLA class II alleles that provides a broad representation of class II HLA allele binding pockets.

Of all the peptide-HLA binding interactions assayed, 50% displayed strong binding affinity (estimated $IC_{50}$<1 μM), 13% showed moderate binding (1 μM<estimated $IC_{50}$<10 μM), 11% showed weak binding affinity (10 μM<estimated $IC_{50}$<100 μM) and 11% exhibited no significant affinity (estimated $IC_{50}$>100 μM) to the target allele. In 18 cases, the data were not sufficient to establish binding affinity.

The concordance of computational predictions and binding assay results was evaluated by classifying peptide-HLA binding pairs as either true positive (TP), false positive (FP), true negative (TN), or false negative (FN). For a given HLA allele, an EpiMatrix Z-score≥1.64 indicates that the peptide is in the top 5% of predicted binders and is considered a 'hit'. The overall predictive success rate was 85%, excluding indeterminate measurements. The correlation between prediction and binding was 82% for DRB*0101, 75% for DRB1*0301, 95% for DRB1*0401, 73% for DRB1*0701, and 100% for DRB1*0801 (FIG. 11). These correlations fall in the range of previously published results for IAV peptides predicted using EpiMatrix and other epitope-mapping tools (Moise L et. al., *Hum. Vaccin. Immunother.*, 9:1598-1607, 2013).

PBMC Isolation

Leukocyte reduction filters were obtained from de-identified healthy donors (Rhode Island Blood Center, Providence, R.I., USA) and buffy coats were obtained from age-identified healthy donors (Research Blood Components, Brighton, Mass., USA). All studies using human blood were performed in accordance with NIH regulations and with the approval of the University of Rhode Island institutional review board.

All leukocyte reduction filters and buffy coats were obtained and processed on the same day as the blood was drawn. Fresh PBMC were isolated from leukocyte reduction filters or buffy coats by Ficoll-Paque density gradient centrifugation (GE Healthcare Biosciences, Pittsburgh, Pa., USA) as follows: leukocyte reduction filters were back-flushed by Hank's Balanced Salt Solution (HBSS) (Cellgro, Manassas, Va., USA) with 2.5% sucrose and 5 mM EDTA (pH=7.2). Buffy coats were removed by a syringe and diluted in Dulbecco's Phosphate-Buffered Saline (DPBS) (Thermo Fisher Scientific, Waltham, Mass., USA). Blood from filters or buffy coats was underlaid with Ficoll (Histopaque 1077) (Sigma-Aldrich, St. Louis, Mo., USA) before centrifugation to isolate mononuclear cells. PBMC were transferred to separate tubes and washed twice in DPBS. PBMC were then re-suspended in cell culture medium: RPMI 1640 (Cellgro, Manassas, Va., USA) with 10% human AB serum (Valley Biomedical, Winchester, Va., USA), 1% L-glutamine (Life Technologies, Carlsbad, Calif., USA) and 0.1% Gentamycin (Cellgro, Manassas, Va., USA).

PBMC Culture

Freshly isolated PBMC were cultured with individual peptides (10 µg/ml) or pools of peptides (10 µg/ml) over eight days at 37° C. under a 5% $CO_2$ atmosphere to expand antigen-specific T cells. Prior to placing the peptides in culture, they were dissolved in DMSO and further diluted in culture medium. The maximum concentration of DMSO per peptide per well was 0.2%. In wells of a 48-well cell culture plate, $2\times10^6$ cells in 150 µl of culture medium were stimulated with 150 µl each individual peptide or pool. Positive control wells received PHA (Thermo Fisher Scientific, Waltham, Mass., USA) at 1 µg/ml or CEFT peptide pool (CTL, Shaker Heights, Ohio, USA) at 10 µg/ml. Negative control wells only received culture medium with 0.2% DMSO. At days three and six, cells were supplemented with 10 ng/ml of IL-2 (BD Pharmingen, San Diego, Calif., USA) by half media replacement. At day eight, PBMC were collected and washed in preparation for antigen re-stimulation to measure cytokine secretion by ELISpot assay. For HLA-DR blocking experiments, PBMC from the same donor were cultured in the presence or absence of 5 µg/ml purified NA/LE® mouse anti-human HLA-DR antibody (BD Pharmingen, San Diego, Calif., USA).

HLA-DR Blocking Assay

To identify whether the peptides were presented by HLA-DR, the effect of an anti-HLA-DR antibody on the epitope-specific T cell responses by IFNγ enzyme-linked immunospot (ELISpot) in three healthy donors was examined. For ten of the peptides (IAV-1, H7N9-2, -4, -7, -9, -12, -13, -14A, 5-HUMAN-A, and —B), peptide-specific spot formation was 100% inhibited by blocking HLA-DR, indicating that these peptides are restricted by HLA-DR (Table 2).

TABLE 2

Inhibition of Peptide-specific Responses by HLA-DR Blocking Antibody

| Peptide Name | % Inhibition by HLA-DR blocking Ab |
|---|---|
| IAV-1 | 100% |
| IAV-2 | 73% |
| IAV-3 | 78% |
| IAV-4 | 96% |
| H7N9-1 | 46% |
| H7N9-2 | 100% |
| H7N9-3 | 97% |
| H7N9-4 | 100% |
| H7N9-5 | N/A |
| H7N9-6 | N/A |
| H7N9-7 | 100% |
| H7N9-8 | 89% |
| H7N9-9 | 100% |
| H7N9-10 | 68% |
| H7N9-11 | increased response |
| H7N9-12 | 100% |
| H7N9-13 | 100% |
| H7N9-14A | 100% |
| H7N9-14B | N/A |
| 5_HUMAN-A | 100% |
| 5-HUMAN-B | 100% |
| 12-HUMAN | N/A |
| 14A-HUMAN | N/A |

PBMC were incubated with H7N9 peptides and controls in the presence or absence of an anti-HLA-DR blocking antibody as described in Methods. Most peptide-specific responses were inhibited by the addition of the antibody, suggesting the peptides were indeed presented by HLA-DR molecules. As the inhibition was not always complete, and in one case (H7N9-11) the response increased in the presence of the blocking antibody, the possibility of presentation by other class II alleles (DP, DQ) and/or class I HLA cannot be ruled out.

N/A: response in absence of blocking Ab was below assay background.

Seven of the peptides (IAV-2, -3, -4, H7N9-1, -3, -8, and -10) induced T cell responses that were only partially inhibited by blocking HLA-DR due to presentation by another HLA molecule such as HLA-DP, HLA-DQ, or class I HLA in addition to, or instead of HLA-DR. Several of the peptides contained class I HLA binding motifs identified by EpiMatrix (EpiVax Providence, R.I., USA). In the case of peptide H7N9-11, response was absent except when HLA-DR was blocked, suggesting that other HLA alleles may present this peptide.

ELISpot Assay

PBMC from eighteen individual healthy donors were stimulated in culture with individual peptides over eight days. Human IFNγ production was measured in response to re-stimulation with individual peptides in ELISpot assays (FIG. 12A) using an IFNγ ELISpot Kit according to the manufacturer's protocol (Mabtech AB, Cincinnati, Ohio, USA). ELISpot assays were performed following the eight-day expansion period because ex vivo responses to the peptides did not rise significantly above background at 24-48 hours suggesting that epitope-specific T cell frequencies were too low to detect without expanding precursor populations. Cells from the were transferred at $1\times10^5$/well or $1.5\times10^5$/well to ELISpot plates that were pre-coated with anti-human IFNγ capture antibody, and re-stimulated with corresponding peptides at 10 µg/ml. Positive control wells were stimulated with PHA at 1 µg/ml or CEFT at 10 µg/ml. Negative controls only received culture medium with DMSO at the same concentration as would be present in peptide-stimulated cultures (0.2%). All stimulations and controls were administered in triplicate wells. ELISpot plates were incubated for 24 hours at 37° C. under a 5% $CO_2$ atmosphere, washed and incubated with a secondary HRP-labeled anti-IFNγ detection antibody, and developed by the addition of TMB substrate. Raw spot counts were recorded using an ImmunoSpot reader; i.e., the CTL S5 UV Analyzer (Cellular Technology Limited, Shaker Heights, Ohio, USA). Responses were considered positive if the number of spots was greater than 50 over background per million PBMC and at least twice the background. The ELISpot SI was determined by dividing the average number of spots in each peptide triplicate by the average number of spots in the negative control wells.

The data were analyzed by calculating the SI (stimulation index) of each response. A significant negative correlation ($p<0.05$) was observed, as shown in FIG. 12B.

Multicolor Flow Cytometry

Approximately, $3\times10^6$ PBMCs were stimulated with individual or pooled peptides at 10 µg/ml, or culture medium with 0.2% DMSO as a negative control in the presence of anti-CD49d and anti-CD28 antibody at 0.5 µg/ml (BD Pharmingen) (BD Biosciences, San Jose, Calif., USA) over eight days. IL-2 (10 ng/ml) was added at days three and six. At day eight, PBMC were re-stimulated with the corresponding peptides at 10 µg/ml or negative control for 24 hours. At day nine, cells were collected and washed in preparation for flow cytometric analysis.

Re-stimulated PBMC were first incubated with fixable viability stain 450 (BD Horizon) (BD Biosciences, San Jose, Calif., USA) for 15 minutes at room temperature. Afterwards, cells were stained with fluorochrome-conjugated anti-human monoclonal antibodies against T cell surface antigens (Alexa Fluor 700 anti-CD3, PerCP-Cy5.5 anti-CD4, APC anti-CD25, and FITC anti-CD39) (BD Pharmingen) (BD Biosciences, San Jose, Calif., USA) for 30 minutes at 4° C. Cells were then fixed and permeabilized by using FoxP3 Fixation/Permeabilization solution, i.e., FoxP3/Transcription Factor Staining Buffer Set (eBioscience, San Diego, Calif., USA) for 30 minutes at room temperature before being stained with PE-conjugated anti-human FoxP3 antibody, i.e., clone 259D/C7 (BD Pharmingen) (BD Biosciences, San Jose, Calif., USA) for at least 30 minutes at room temperature. Cells were washed with FoxP3 Permeabilization Buffer (eBioscience, San Diego, Calif., USA) and acquired by flow cytometry using a Beckton-Dickinson LSR-II flow cytometer (BD Biosciences, San Jose, Calif., USA). Data were analyzed in FlowJo software (Treestar, Ashland, Oreg., USA).

T Cell Reactivity of Pooled Peptides

Figure 13:
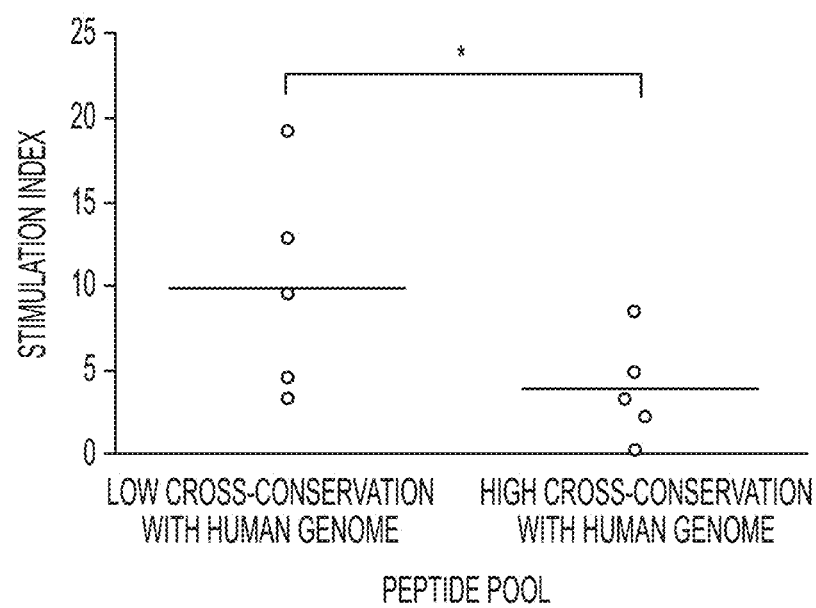
FIG. 13 is a graph showing Human IFNγ responses to pooled H7N9 peptides.

To relate the observation described above more specifically to H7N9 infection and/or vaccination, the same experiment was performed with two peptide pools (FIG. 13). The first pool was comprised of H7N9 ICS peptides with JanusMatrix Delta values between 10 and 20 (H7N9-4 to -12). The second pool contained peptides with JanusMatrix Delta values higher than 20 (H7N9-13 to -14B). Because there were more peptides in the first pool than the second, the pool concentrations were equalized to achieve the same total per unit of volume. The SI of the second pool, consisting of the most human-like H7N9 peptides, was significantly lower than the first pool ($p<0.05$). These results reflect the average responses of five donors. Peptides were pooled into groups according to their predicted immunological properties, based on their similarity to circulating IAV, cross-conservation with human sequences, or status as self-antigens and the results were consistent with those observed for the individual peptides in the pools.

Treg Phenotyping

Peptides were also tested individually for their ability to expand Tregs in healthy donor PBMC. All three peptides with JanusMatrix Delta values greater than 20 induced the expansion of significantly higher proportions of CD3$^+$CD4$^+$FoxP3$^+$ T cells in vitro (n=3) (FIG. 14B, $p<0.05$) than culture medium. Similar trends in the frequency of CD25$^+$FoxP3$^+$ and CD39$^+$FoxP3$^+$ Tregs in assays performed in parallel were observed, although only the increase in CD39$^+$FoxP3$^+$ frequency was statistically significant. Pooled influenza A epitopes did not induce a similar expansion of CD25$^+$FoxP3$^+$ and CD39$^+$FoxP3$^+$ T cells in vitro (n=9).

Bystander Suppression

Bystander suppression experiments were performed to determine whether a peptide with known HLA promiscuity and a human TCR signature could exert a regulatory effect on adjacent inflammatory responses as may occur in natural infection or vaccination. Normal subject PBMC were stimulated with a pool of H7N9 ICS peptides (including all except H7N9-1, -2, -9, and -13) in the presence or absence of peptide H7N9-13, the H7 homolog of the seasonal influenza HA immunodominant epitope having a JanusMatrix Delta value of 21.85. To ensure that the pool was not diluted by the addition of H7N9-13, the concentrations were adjusted so that both cultures had the same absolute concentration of the pooled peptides with the addition of H7N9-13 being the only variable. Co-incubation with H7N9-13 significantly suppressed T cell response to the pooled peptides (n=7) (FIG. 15A, $p<0.01$). In contrast, co-incubation with peptide H7N9-9, which is not as cross-conserved with the human genome as H7N9-13, did not suppress T cell responses to the pool of H7N9 epitopes (n=4) (FIG. 15B) suggesting that the immunosuppressive activity of H7N9-13 is peptide-specific.

To confirm the effect using peptides from other IAV strains, the same experiment was performed using individual or pooled peptides from the HA of circulating IAV strains (IAV-1 through -4) or an H7N9 peptide from M1 with high similarity to the sequence of circulating IAV strains (H7N9-3). Using PBMC from two individual donors, peptide H7N9-13 significantly suppressed T cell response to IAV-3 when co-cultured with H7N9-3 as compared to responses to IAV-3 in the absence of H7N9-3, similar reductions in T cell responses were observed to peptide IAV-1 in the first donor and IAV-2 in the second when H7N9-3 was present (FIG. 15C, all $p<0.05$). Reduced responses to the pool of IAV peptides (1-4) were also observed in the presence of H7N9-13, -14A and -14B, which also had high JanusMatrix Delta scores (>20) though not statistically significant.

Statistical Analysis

Tests to determine p-value and statistical significance were performed using Graphpad Prism (GraphPad Software, Inc., La Jolla, Calif., USA) or Microsoft Excel (Microsoft Corporation, Redmond, Wash., USA). When correlating JanusMatrix Delta with SI, the Pearson function was used to determine the R. Student's t-test was used to calculate statistical significance between paired or unpaired T cell reactivity values.

HLA DR3 Mouse Immunizations

Figure 16:
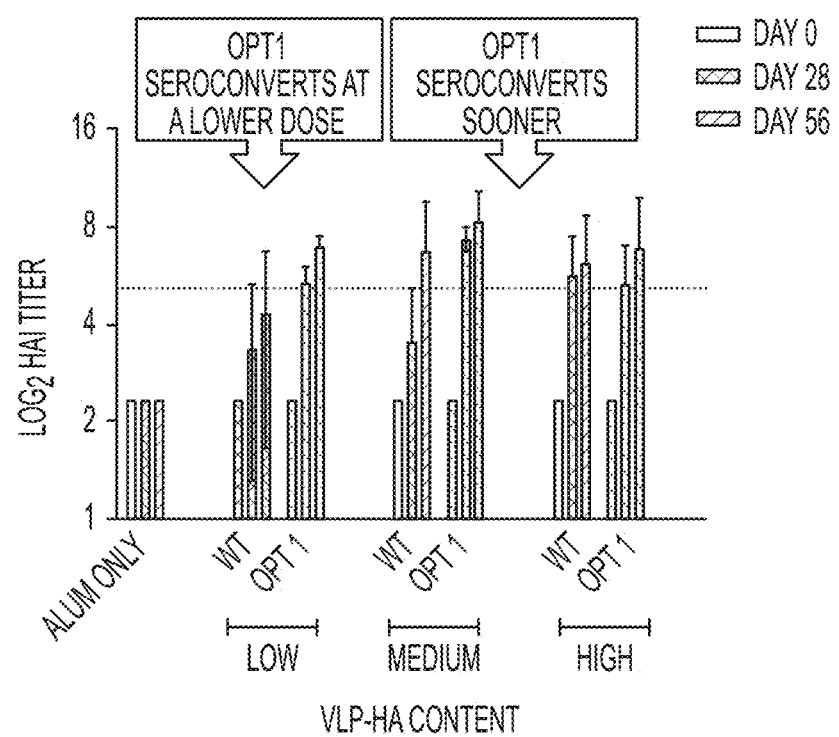
FIG. 16 depicts the protective levels of HAI antibodies stimulated by Opt1 H7N9 VLP vaccine in HLA DR3 transgenic mice.

Groups of 6 female HLA DR3 transgenic mice, 6-8 weeks old, were intramuscularly primed and boosted four weeks thereafter with either A/Shanghai/2/2013 (H7N9) virus-like particles composed of the wild-type hemagglutinin (FIG. 3), neuraminidase and matrix proteins or virus-like particles composed of the same neuraminidase and matrix proteins formulated with cluster 321-engineered A/Shanghai/2/2013 (H7N9) hemagglutinin (FIG. 2). Virus-like particles were produced in a mammalian cell culture expression system (HEK 293T cells) transiently transfected with plasmids expressing influenza matrix protein (M1), neuraminidase, hemagglutinin or engineered hemagglutinin. Cell culture supernatants were collected and VLPs purified via ultracentrifugation. Vaccine dosage according to HA content was based on protein concentration. Mice were immunized with HA at either 0.12 μg (low), 0.6 μg (medium) or 3 μg (high) per dose. Both the wild type and engineered immunogens were co-formulated with Imject Alum adjuvant. Serum was collected prior to each immunization and four weeks following the boost immunization for measurement of neutralizing antibody activity by hemagglutination inhibition assay. Mice immunized with cluster 321-engineered A/Shanghai/2/2013 virus-like particle vaccine developed protective levels of hemagglutination inhibiting antibodies, suggesting that modifications of H7-HA preserved neutralizing epitopes. Additionally, cluster 321-engineered A/Shanghai/2/2013 virus-like particle vaccine raised hemagglutination inhibiting antibodies sooner and at lower doses than wild-type virus-like particle vaccine (FIG. 16).

Hemagglutination Inhibition Assay

The HAI assay was used to assess functional antibodies to the HA able to inhibit agglutination of horse erythrocytes. The protocol was adapted from the CDC laboratory-based influenza surveillance manual. To inactivate non-specific inhibitors, sera were treated with receptor destroying enzyme (RDE) (Denka Seiken, Co., Tokyo, JP) prior to being tested. Three parts RDE was added to one part sera and incubated overnight at 37° C. RDE was inactivated by incubation at 56° C. for approximately 30 minutes. RDE treated sera was two-fold serially diluted in v-bottom microtiter plates. An equal volume of reassortant virus, adjusted to approximately 8 HAU/50 was added to each well. The reassortant viruses contained the internal genes from the mouse adapted strain A/Puerto Rico/8/1934 and the surface proteins HA and NA from A/Shanghai/2/2013. The plates were covered and incubated at room temperature for 20 minutes followed by the addition of 1% horse erythrocytes (HRBC) (Lampire Biologicals, Pipersville, Pa., USA) in PBS. Red blood cells were stored at 4° C. and used within 72 hours of preparation. The plates were mixed by agitation, covered, and the RBCs were allowed to settle for 1 hour at room temperature. The HAI titer was determined by the reciprocal dilution of the last well which contained non-agglutinated RBC. Positive and negative serum controls were included for each plate.

In some embodiments, the H7 polypeptide or polypeptide of FIG. 2 can differ in amino acid sequence by one or more substitutions, deletions, insertions, inversions, fusions, and truncations or a combination of any of these. A variant polypeptide can differ in amino acid sequence by one or more substitutions, deletions, insertions, inversions, fusions, and truncations or a combination of any of these. Variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions can positively or negatively affect function to some degree. Non-functional variants typically contain one or more non-conservative amino acid substitutions, deletions, insertions, inversions, or truncation or a substitution, insertion, inversion, or deletion in a critical residue or critical region.

The present technology also encompasses polypeptides having a lower degree of identity but having sufficient similarity so as to perform one or more of the same functions performed by a polypeptide encoded by a nucleic acid molecule of the present technology. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found, for example, in Bowie, J. et al., *Science,* 247:1306-1310, 1990.

As used herein, two polypeptides (or a region of the polypeptides) are substantially homologous or identical when the amino acid sequences are at least about 45-55%, typically at least about 70-75%, more typically at least about 80-85%, and more typically greater than about 90% or more homologous or identical. To determine the percent homology or identity of two amino acid sequences, or of two nucleic acid sequences, the sequences are aligned for optimal comparison purposes (e.g., gaps can be introduced in the sequence of one polypeptide or nucleic acid molecule for optimal alignment with the other polypeptide or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (e.g., percent homology equals the number of identical positions/total number of positions×100).

In some embodiments, the present technology includes polypeptide fragments of the polypeptides of the invention. In some embodiments, the present technology encompasses fragments of the variants of the polypeptides described herein. As used herein, a fragment comprises at least about five contiguous amino acids. Useful fragments include those that retain one or more of the biological activities of the polypeptide as well as fragments that can be used as an immunogen to generate polypeptide-specific antibodies. Biologically active fragments are, for example, about 6, 9, 12, 15, 16, 20 or 30 or more amino acids in length. Fragments can be discrete (not fused to other amino acids or polypeptides) or can be within a larger polypeptide. Several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

In some embodiments, the present technology provides chimeric or fusion polypeptides. These comprise a polypeptide of the invention operatively linked to a heterologous protein or polypeptide having an amino acid sequence not substantially homologous to the polypeptide. "Operatively linked" indicates that the polypeptide and the heterologous protein are fused in-frame.

In some embodiments, the isolated polypeptide can be purified from cells that naturally express it, purified from cells that have been altered to express it (recombinant), or synthesized using known protein synthesis methods. In some embodiments, the present technology the polypeptide is produced by recombinant DNA techniques. By way of example, but not by way of limitation, a nucleic acid molecule encoding the polypeptide is cloned into an expression vector, the expression vector introduced into a host cell and the polypeptide expressed in the host cell. The polypeptide can then be isolated from the cells by an appropriate purification scheme using standard protein purification techniques.

In some embodiments, the polypeptides can include, for example, modified forms of naturally occurring amino acids such as D-stereoisomers, non-naturally occurring amino acids; amino acid analogs; and mimetics.

The vaccines of the present invention avoid peptide aggregation and retain biological activities prior to and after administration. The vaccines of the present invention typically are ready to administer, aqueous solutions which are sterile, storage-stable and pharmaceutically acceptable without the need for reconstitution prior to administration. The vaccines of the present invention are suitable for administration to a subject which means that they are pharmaceutically acceptable, non-toxic, do not contain any components which would adversely affect the biological or hormonal effects of the peptide.

The claimed vaccines are typically stored in a sealed container, vial or cartridge which is typically suitable for long term storage. "Suitable for long-term storage" means that the vial, container or cartridge does not allow for the escape of components or the ingress of external components, such as, microorganisms during long period of storage.

The vaccines of the present invention are preferably administered by injection, typically intramuscular injection.

The vaccines of the present invention, can be stored in single-dose or multi-dose sealed containers, vials or cartridges. The sealed container, vial or cartridge is typically suitable for use with a single or multi-dose injection pen or drug delivery device. The sealed container can comprise one or more doses of the vaccines of the present invention, wherein each dose comprises an effective amount of the vaccine as described herein.

A single-dose injection pen, or drug delivery device is typically a disposable device which uses a sealed container which comprises a single dose of an effective amount of a vaccine described herein. A multi-dose injection pen or drug delivery device typically contains more than one dose of an effective amount of a vaccine thereof in the pharmaceutical compositions described herein. The multi-dose pen can typically be adjusted to administer the desired volume of the storage stable vaccines described herein. In certain embodiment the multi-dose injection pen prevents the ingress of microbial contaminants from entering the container or cartridge which can occur through multiple uses of one needle.

As used herein, an effective amount refers to an amount sufficient to elicit the desired response. In the present invention, the desired biological response includes producing antibodies against a pathogen, in particular against influenza A/Shanghai/2/2013.

The subject as used herein can be an animal, for example, a mammal, such as a human.

What is claimed is:

1. A polypeptide comprising the entire amino acid sequence of SEQ ID NO: 2 or a fragment thereof provided that said fragment contains SEQ ID NO: 3.

2. A vaccine comprising one or more polypeptides comprising the entire amino acid sequence of SEQ ID NO: 2 or a fragment thereof provided that said fragment contains SEQ ID NO: 3.

3. The vaccine of claim 2, further comprising an adjuvant.

4. A composition comprising one or more polypeptides comprising the entire amino acid sequence of SEQ ID NO: 2 or a fragment thereof provided that said fragment contains SEQ ID NO: 3.

5. A method for vaccinating against influenza comprising administering to a subject a composition comprising one or more polypeptides comprising the entire amino acid sequence of SEQ ID NO: 2 or a fragment thereof provided that said fragment contains SEQ ID NO: 3.

6. The method of claim 5, wherein the composition further comprises an adjuvant.

7. The method of claim 5, wherein the influenza is avian-origin H7N9 influenza.

8. A method for enhancing an anti-H7 antibody response comprising administering a composition comprising one or more polypeptides comprising the entire amino acid sequence of SEQ ID NO: 2 or a fragment thereof provided that said fragment contains SEQ ID NO: 3.

9. The method of claim 8, wherein the composition further comprises an adjuvant.

10. A kit for enhancing an anti-H7 antibody response in a subject, said kit comprising one or more polypeptides comprising the amino acid sequence of SEQ ID NO: 2 or a fragment thereof provided that said fragment contains SEQ ID NO: 3.

11. The kit of claim 10, further comprising an adjuvant.

* * * * *

SEQUENCE LISTING

<160> NUMBER OF SEQ ID NOS: 55

<210> S

```
Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
            115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
                180                 185                 190

His Ser Val Ser Thr Ala Glu Gln Thr Lys Leu Tyr Gly Ser Gly Asn
            195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asn Cys Glu Gly
            275                 280                 285

Asp Cys Tyr His Ser Gly Gly Thr Ile Ile Ser Asn Leu Pro Phe Gln
290                 295                 300

Asn Ile Asp Ser Arg Ala Val Gly Lys Cys Pro Arg Tyr Val Lys Gln
305                 310                 315                 320

Asn Thr Leu Lys Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
            370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
                435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
```

```
                    500                 505                 510
Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
            530                 535                 540

Val Phe Ile Cys Val Lys Asn Gly Asn Met Arg Cys Thr Ile Cys Ile
545                 550                 555                 560

<210> SEQ ID NO 3
<211> LENGTH: 21
<212> TYPE: PRT
<213> ORGANISM: Influenza A virus

<400> SEQUENCE: 3

Cys Pro Arg Tyr Val Lys Gln Asn Thr Leu Lys Leu Ala Thr Gly Met
1               5                   10                  15

Lys Asn Val Pro Glu
            20

<210> SEQ ID NO 4
<211> LENGTH: 560
<212> TYPE: PRT
<213> ORGANISM: Influenza A virus

<400> SEQUENCE: 4

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
```

245                 250                 255
Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
        290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
450                 455                 460

Leu Arg Glu Asn Ala Glu Asp Gly Thr Gly Cys Phe Glu Ile Phe
465                 470                 475                 480

His Lys Cys Asp Asp Cys Met Ala Ser Ile Arg Asn Asn Thr Tyr
            485                 490                 495

Asp His Ser Lys Tyr Arg Glu Glu Ala Met Gln Asn Arg Ile Gln Ile
        500                 505                 510

Asp Pro Val Lys Leu Ser Ser Gly Tyr Lys Asp Val Ile Leu Trp Phe
    515                 520                 525

Ser Phe Gly Ala Ser Cys Phe Ile Leu Leu Ala Ile Val Met Gly Leu
        530                 535                 540

Val Phe Ile Cys Val Lys Asn Gly Asn Met Arg Cys Thr Ile Cys Ile
545                 550                 555                 560

<210> SEQ ID NO 5
<211> LENGTH: 21
<212> TYPE: PRT
<213> ORGANISM: Influenza A virus

<400> SEQUENCE: 5

Cys Pro Arg Tyr Val Lys Gln Arg Ser Leu Leu Leu Ala Thr Gly Met
1               5                   10                  15

Lys Asn Val Pro Glu
            20

<210> SEQ ID NO 6
<211> LENGTH: 21
<212> TYPE: PRT
<213> ORGANISM: Influenza A virus -continued

```
<400> SEQUENCE: 6

Cys Pro Arg Tyr Val Lys Gln Asn Thr Leu Lys Leu Ala Thr Gly Met
1               5                   10                  15
Lys Asn Val Pro Glu
            20

<210> SEQ ID NO 7
<211> LENGTH: 9
<212> TYPE: PRT
<213> ORGANISM: Influenze A virus

<400> SEQUENCE: 7

Cys Pro Arg Tyr Val Lys Gln Arg Ser
1               5

<210> SEQ ID NO 8
<211> LENGTH: 9
<212> TYPE: PRT
<213> ORGANISM: Influenza A virus

<400> SEQUENCE: 8

Pro Arg Tyr Val Lys Gln Arg Ser Leu
1               5

<210> SEQ ID NO 9
<211> LENGTH: 9
<212> TYPE: PRT
<213> ORGANISM: Influenza A virus

<400> SEQUENCE: 9

Arg Tyr Val Lys Gln Arg Ser Leu Leu
1               5

<210> SEQ ID NO 10
<211> LENGTH: 9
<212> TYPE: PRT
<213> ORGANISM: Influenza A virus

<400> SEQUENCE: 10

Tyr Val Lys Gln Arg Ser Leu Leu Leu
1               5

<210> SEQ ID NO 11
<211> LENGTH: 9
<212> TYPE: PRT
<213> ORGANISM: Influenza A virus

<400> SEQUENCE: 11

Val Lys Gln Arg Ser Leu Leu Leu Ala
1               5

<210> SEQ ID NO 12
<211> LENGTH: 9
<212> TYPE: PRT
<213> ORGANISM: Influenza A virus

<400> SEQUENCE: 12

Lys Gln Arg Ser Leu Leu Leu Ala Thr
1               5

<210> SEQ ID NO 13
<211> LENGTH: 9
<212> TYPE: PRT
<213> ORGANISM: Influenza A virus
```

```
<400> SEQUENCE: 13

Gln Arg Ser Leu Leu Leu Ala Thr Gly
1               5

<210> SEQ ID NO 14
<211> LENGTH: 9
<212> TYPE: PRT
<213> ORGANISM: Influenza A virus

<400> SEQUENCE: 14

Arg Ser Leu Leu Leu Ala Thr Gly Met
1               5

<210> SEQ ID NO 15
<211> LENGTH: 9
<212> TYPE: PRT
<213> ORGANISM: Influenza A virus

<400> SEQUENCE: 15

Ser Leu Leu Leu Ala Thr Gly Met Lys
1               5

<210> SEQ ID NO 16
<211> LENGTH: 9
<212> TYPE: PRT
<213> ORGANISM: Influenza A virus

<400> SEQUENCE: 16

Leu Leu Leu Ala Thr Gly Met Lys Asn
1               5

<210> SEQ ID NO 17
<211> LENGTH: 9
<212> TYPE: PRT
<213> ORGANISM: Influenza A virus

<400> SEQUENCE: 17

Leu Leu Ala Thr Gly Met Lys Asn Val
1               5

<210> SEQ ID NO 18
<211> LENGTH: 9
<212> TYPE: PRT
<213> ORGANISM: Influenza A virus

<400> SEQUENCE: 18

Leu Ala Thr Gly Met Lys Asn Val Pro
1               5

<210> SEQ ID NO 19
<211> LENGTH: 9
<212> TYPE: PRT
<213> ORGANISM: Influenza A virus

<400> SEQUENCE: 19

Ala Thr Gly Met Lys Asn Val Pro Glu
1               5

<210> SEQ ID NO 20
<211> LENGTH: 9
<212> TYPE: PRT
<213> ORGANISM: Influenza A virus

<400> SEQUENCE: 20
```

Cys Pro Arg Tyr Val Lys Gln Asn Thr
1               5

<210> SEQ ID NO 21
<211> LENGTH: 9
<212> TYPE: PRT
<213> ORGANISM: Influenza A virus

<400> SEQUENCE: 21

Pro Arg Tyr Val Lys Gln Asn Thr Leu
1               5

<210> SEQ ID NO 22
<211> LENGTH: 9
<212> TYPE: PRT
<213> ORGANISM: Influenza A virus

<400> SEQUENCE: 22

Arg Tyr Val Lys Gln Asn Thr Leu Lys
1               5

<210> SEQ ID NO 23
<211> LENGTH: 9
<212> TYPE: PRT
<213> ORGANISM: Influenza A virus

<400> SEQUENCE: 23

Tyr Val Lys Gln Asn Thr Leu Lys Leu
1               5

<210> SEQ ID NO 24
<211> LENGTH: 9
<212> TYPE: PRT
<213> ORGANISM: Influenza A virus

<400> SEQUENCE: 24

Val Lys Gln Asn Thr Leu Lys Leu Ala
1               5

<210> SEQ ID NO 25
<211> LENGTH: 9
<212> TYPE: PRT
<213> ORGANISM: Influenza A virus

<400> SEQUENCE: 25

Lys Gln Asn Thr Leu Lys Leu Ala Thr
1               5

<210> SEQ ID NO 26
<211> LENGTH: 9
<212> TYPE: PRT
<213> ORGANISM: Influenza A virus

<400> SEQUENCE: 26

Gln Asn Thr Leu Lys Leu Ala Thr Gly
1               5

<210> SEQ ID NO 27
<211> LENGTH: 9
<212> TYPE: PRT
<213> ORGANISM: Influenza A virus

<400> SEQUENCE: 27

Asn Thr Leu Lys Leu Ala Thr Gly Met

<210> SEQ ID NO 28
<211> LENGTH: 9
<212> TYPE: PRT
<213> ORGANISM: Influenza A virus

<400> SEQUENCE: 28

Thr Leu Lys Leu Ala Thr Gly Met Lys
1               5

<210> SEQ ID NO 29
<211> LENGTH: 9
<212> TYPE: PRT
<213> ORGANISM: Influenza A virus

<400> SEQUENCE: 29

Leu Lys Leu Ala Thr Gly Met Lys Asn
1               5

<210> SEQ ID NO 30
<211> LENGTH: 9
<212> TYPE: PRT
<213> ORGANISM: Influenza A virus

<400> SEQUENCE: 30

Lys Leu Ala Thr Gly Met Lys Asn Val
1               5

<210> SEQ ID NO 31
<211> LENGTH: 14
<212> TYPE: PRT
<213> ORGANISM: Influenza A virus

<400> SEQUENCE: 31

Pro Lys Tyr Val Lys Ser Thr Lys Leu Arg Leu Ala Thr Gly
1               5                   10

<210> SEQ ID NO 32
<211> LENGTH: 14
<212> TYPE: PRT
<213> ORGANISM: Influenza A virus

<400> SEQUENCE: 32

Pro Arg Tyr Val Lys Gln Ser Thr Leu Lys Leu Ala Thr Gly
1               5                   10

<210> SEQ ID NO 33
<211> LENGTH: 14
<212> TYPE: PRT
<213> ORGANISM: Influenza A virus

<400> SEQUENCE: 33

Pro Arg Tyr Val Lys Gln Asn Thr Leu Lys Leu Ala Thr Gly
1               5                   10

<210> SEQ ID NO 34
<211> LENGTH: 14
<212> TYPE: PRT
<213> ORGANISM: Influenza A virus

<400> SEQUENCE: 34

Pro Lys Tyr Val Lys Ser Asn Arg Leu Val Leu Ala Thr Gly
1               5                   10

<210> SEQ ID NO 35
<211> LENGTH: 18
<212> TYPE: PRT
<213> ORGANISM: Influenza A virus

<400> SEQUENCE: 35

Arg Ile Asp Phe His Trp Leu Met Leu Asn Pro Asn Asp Thr Val Thr
1               5                   10                  15

Phe Ser

<210> SEQ ID NO 36
<211> LENGTH: 18
<212> TYPE: PRT
<213> ORGANISM: Influenza A virus

<400> SEQUENCE: 36

Tyr Ala Glu Met Lys Trp Leu Leu Ser Asn Thr Asp Asn Ala Ala Phe
1               5                   10                  15

Pro Gln

<210> SEQ ID NO 37
<211> LENGTH: 19
<212> TYPE: PRT
<213> ORGANISM: Influenza A virus

<400> SEQUENCE: 37

Lys Gly Ile Leu Gly Phe Val Phe Thr Leu Thr Val Pro Ser Glu Arg
1               5                   10                  15

Gly Leu Gln

<210> SEQ ID NO 38
<211> LENGTH: 19
<212> TYPE: PRT
<213> ORGANISM: Influenza A virus

<400> SEQUENCE: 38

Gln Pro Glu Trp Phe Arg Asn Val Leu Ser Ile Ala Pro Ile Met Phe
1               5                   10                  15

Ser Asn Lys

<210> SEQ ID NO 39
<211> LENGTH: 14
<212> TYPE: PRT
<213> ORGANISM: Influenza A virus

<400> SEQUENCE: 39

Gly Phe Thr Lys Arg Thr Ser Gly Ser Ser Val Lys Arg Glu
1               5                   10

<210> SEQ ID NO 40
<211> LENGTH: 18
<212> TYPE: PRT
<213> ORGANISM: Influenza A virus

<400> SEQUENCE: 40

Arg Arg Asp Gln Lys Ser Leu Arg Gly Arg Ser Ser Thr Leu Gly Leu
1               5                   10                  15

Asp Ile

<210> SEQ ID NO 41
<211> LENGTH: 17

```
<212> TYPE: PRT
<213> ORGANISM: Influenza A virus

<400> SEQUENCE: 41

Asn Tyr Leu Leu Thr Trp Lys Gln Val Leu Ala Glu Leu Gln Asp Ile
1               5                   10                  15

Glu

<210> SEQ ID NO 42
<211> LENGTH: 18
<212> TYPE: PRT
<213> ORGANISM: Influenza A virus

<400> SEQUENCE: 42

Asp Lys Leu Tyr Glu Arg Val Lys Arg Gln Leu Arg Glu Asn Ala Glu
1               5                   10                  15

Glu Asp

<210> SEQ ID NO 43
<211> LENGTH: 17
<212> TYPE: PRT
<213> ORGANISM: Influenza A virus

<400> SEQUENCE: 43

Ala Val Lys Leu Tyr Lys Lys Leu Lys Arg Glu Met Thr Phe His Gly
1               5                   10                  15

Ala

<210> SEQ ID NO 44
<211> LENGTH: 18
<212> TYPE: PRT
<213> ORGANISM: Influenza A virus

<400> SEQUENCE: 44

Ala Ala Asn Ile Ile Gly Ile Leu His Leu Ile Leu Trp Ile Leu Asp
1               5                   10                  15

Arg Leu

<210> SEQ ID NO 45
<211> LENGTH: 18
<212> TYPE: PRT
<213> ORGANISM: Influenza A virus

<400> SEQUENCE: 45

Ser Arg Lys Leu Leu Leu Ile Val Gln Ala Leu Arg Asp Asn Leu Glu
1               5                   10                  15

Pro Gly

<210> SEQ ID NO 46
<211> LENGTH: 15
<212> TYPE: PRT
<213> ORGANISM: Influenza A virus

<400> SEQUENCE: 46

Gln Ile Thr Phe Met Gln Ala Leu Gln Leu Leu Leu Glu Val Glu
1               5                   10                  15

<210> SEQ ID NO 47
<211> LENGTH: 14
<212> TYPE: PRT
<213> ORGANISM: Influenza A virus
```

```
<400> SEQUENCE: 47

Pro Arg Tyr Val Lys Gln Arg Ser Leu Leu Leu Ala Thr Gly
1               5                   10

<210> SEQ ID NO 48
<211> LENGTH: 15
<212> TYPE: PRT
<213> ORGANISM: Influenza A virus

<400> SEQUENCE: 48

Ile Val Tyr Trp Lys Gln Trp Leu Ser Leu Lys Asn Leu Thr Gln
1               5                   10                  15

<210> SEQ ID NO 49
<211> LENGTH: 16
<212> TYPE: PRT
<213> ORGANISM: Influenza A virus

<400> SEQUENCE: 49

Trp Lys Gln Trp Leu Ser Leu Lys Asn Thr Leu Thr Gln Gly Ser Leu
1               5                   10                  15

<210> SEQ ID NO 50
<211> LENGTH: 15
<212> TYPE: PRT
<213> ORGANISM: Influenza A virus

<400> SEQUENCE: 50

Leu Ser Gly Leu Lys Arg Ala Ser Ala Ser Ser Leu Arg Ser Ile
1               5                   10                  15

<210> SEQ ID NO 51
<211> LENGTH: 15
<212> TYPE: PRT
<213> ORGANISM: Influenza A virus

<400> SEQUENCE: 51

Arg Gly Ile Leu Lys Arg Asn Ser Ser Ser Ser Thr Asp Ser
1               5                   10                  15

<210> SEQ ID NO 52
<211> LENGTH: 15
<212> TYPE: PRT
<213> ORGANISM: Influenza A virus

<400> SEQUENCE: 52

Val Arg His Phe Met Gln Ser Leu Ala Leu Leu Met Ser Pro Val
1               5                   10                  15

<210> SEQ ID NO 53
<211> LENGTH: 15
<212> TYPE: PRT
<213> ORGANISM: Influenza A virus

<400> SEQUENCE: 53

Glu Glu Asp Leu Lys Gln Leu Leu Ala Leu Lys Gly Ser Ser Tyr
1               5                   10                  15

<210> SEQ ID NO 54
<211> LENGTH: 15
<212> TYPE: PRT
<213> ORGANISM: Influenza A virus

<400> SEQUENCE: 54
```

```
Asn Leu Glu Leu Leu Ser Leu Lys Arg Leu Thr Leu Thr Thr Ser
1               5                   10                  15

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Phe Thr Leu Ser Ser Ser Thr Ile Ser
1               5
```